United States Patent [19]
Birnbaumer et al.

[11] Patent Number: 5,932,417
[45] Date of Patent: Aug. 3, 1999

[54] METHOD OF SCREENING COMPOUNDS FOR CONTROLLING CAPACITATIVE CALCIUM ION ENTRY INTO MAMMALIAN CELLS

[75] Inventors: Lutz Birnbaumer; Xi Zhu, both of Los Angeles, Calif.

[73] Assignee: The Regents of the University of California, Oakland, Calif.

[21] Appl. No.: 08/729,955

[22] Filed: Oct. 15, 1996

[51] Int. Cl.⁶ .............................. C12Q 1/68; C12N 15/00; C12N 15/85; C07H 21/04
[52] U.S. Cl. .......................... 435/6; 435/69.1; 435/172.3; 435/325; 435/375; 536/23.1; 536/24.5
[58] Field of Search .................................. 435/4, 6, 69.1, 435/325, 172.3, 375; 536/23.1, 24.5; 514/44

[56] References Cited

U.S. PATENT DOCUMENTS 5,670,330  9/1997  Sonenberg et al. ..................... 435/15

OTHER PUBLICATIONS

Vaca et al., Activation of recombinant trp by thapsigargin in sf9 insect cells, American Journal of Physiology, vol. 267 (5, pt.1), pp. c1501–1505, 1994.

Verma et al., Gene therapy–promises, problems and prospects, Nature, vol. 389, pp. 239–242, Sep. 18, 1997.

Zhu et al., Molecular cloning of a widely expressed human homologue for the Drosophila trp gene, FEBS Letters, vol. 373, pp. 193–198, Oct. 1995.

Mulligan, The basic science of gene therapy, Science, vol. 260, pp. 926–932, May 14, 1993.

Wes et al., TRPC1, a human homolog of a Drosophila store–operated channel, Proc. Natl. Acad. Sci., vol. 92, pp. 9652–9656, Oct. 1995.

*Primary Examiner*—John L. LeGuyader
*Assistant Examiner*—Andrew Wang
*Attorney, Agent, or Firm*—Oppenheimer Wolff & Donnelly LLP

[57] ABSTRACT

A method for controlling capacitative calcium ion entry into a mammalian cell. The method is based on the discovery that mammalian transient receptor potential (trp) protein are essential for calcium ion entry. Two human trp proteins are disclosed. Htrp1 and Htrp3. The method involves treating cells with a trp-control agent to either raise or lower the amount of biologically active trp protein associated with the cell to thereby control capacitative calcium ion entry into the cell. Screening methods are also disclosed based upon using mammalian trp protein as a screening target.

3 Claims, 3 Drawing Sheets

METHOD OF SCREENING COMPOUNDS FOR CONTROLLING CAPACITATIVE CALCIUM ION ENTRY INTO MAMMALIAN CELLS

This invention was made with government support under Grant No. HL-45198 from the National Institutes of Health. The Government has certain rights in this invention.

BACKGROUND OF THE INVENTION

1. Field of the Invention

The present invention relates generally to the capacitative entry of calcium ions ($Ca^{2+}$) into mammalian cells and the mechanisms by which such capacitative entry is accomplished. More particularly, the present invention is directed to the discovery of transient receptor potential (trp) proteins which are an essential part of the capacitative $Ca^{2+}$ entry (CCE) mechanism in mammalian cells. The invention further relates to methods for altering CCE in mammalian cells by controlling the expression of trp proteins or treating the cell with compounds which inhibit the biological activity of the trp protein. The invention also is directed to using the trp proteins as screening agents in methods for identifying compounds which may be useful in controlling CCE in mammalian cells.

2. Description of Related Art

The publications and other reference materials referred to herein to describe the background of the invention and to provide additional details regarding its practice are hereby incorporated by reference. For convenience, the reference materials are numerically referenced and identified in the appended bibliography. The bibliography also includes a number of references which are not specifically referred to in the description. These references are listed as providing additional description of related art.

Calcium regulation plays an important role in many cellular processes. In non-excitable mammalian cells, activation of phosphoinositide-specific phospholipase C (PLC) produces inositol 1,4,5-trisphosphate ($IP_3$), which in turn causes the release of intracellular calcium from its storage pools in the endoplasmic reticulum. This results in a transient elevation of cytosolic free $Ca^{2+}$, which is normally followed by a $Ca^{2+}$ influx from the extracellular space. By refilling the pools, $Ca^{2+}$ influx plays an important role in prolonging the $Ca^{2+}$ signal, allowing for localized signaling, and maintaining $Ca^{2+}$ oscillations [1].

Calcium influx in non-excitable cells is thought to occur through plasma membrane channels which, in contrast to the voltage-dependent $Ca^{2+}$ channels in excitable cells, are operated not by changes of membrane potentials but rather by how full the internal $Ca^{2+}$ stores are [2]. The $Ca^{2+}$ channels have variously been referred to as calcium release-activated calcium channels (CRACs), store-operated calcium channels (SOCs), and receptor-operated calcium channels (ROCs) (23, 24, 25 and 26). Because the entering $Ca^{2+}$ replenishes $Ca^{2+}$ stores that act like capacitors, it is also called capacitative $Ca^{2+}$ entry or CCE (27, 28).

Although studies using either fluorescent $Ca^{2+}$ indicators or electrophysiological techniques have suggested that multiple types of $Ca^{2+}$ permeant channels may be involved in different cell types to fulfill the influx function, the molecular structure of the channels and the mechanism that regulates the influx have remained unclear and represent one of the major unanswered questions of cellular $Ca^{2+}$ homeostasis [3–5].

Candidates involved in voltage independent $Ca^{2+}$ entry into cells include a gene product missing in a Drosophila mutant, the transient receptor potential (trp), and its homologue, trp-like (trp1). The insect phototransduction pathway is mediated through the activation of PLC coupled by a $G_q$ type protein [6]. The consequent generation of $IP_3$ and the release of $Ca^{2+}$ from its intracellular storage pools is believed to lead to the opening of a light sensitive ion channel and generation of a depolarizing receptor potential. Similar to intracellular $Ca^{2+}$ changes in mammalian cells following stimulation by agonists acting via PLC, electroretinograms of Drosophila eyes are biphasic with an initial peak followed by a sustained phase of which the latter is dependent on extracellular $Ca^{2+}$. This sustained phase is absent in the trp mutant which was therefore proposed to be caused by a defect in the $Ca^{2+}$ influx pathway [6]. The trp gene was cloned [7,8]. Subsequently, molecular cloning of a Drosophila calmodulin binding protein showed it to be a homologue of the trp gene product and named trp-like or trp1 [9]. A detailed analysis of the trp1 sequence showed that it shares moderate homology with voltage-dependent $Ca^{2+}$ and $Na^+$ channels at their putative transmembrane regions. However, in clear contrast with the voltage-dependent channels, it lacks the positively charged amino acid residues at the presumed S4 segment which are thought to act as voltage sensors that promote gating in response to changes in membrane potentials. The structural homology to $Ca^{2+}$ and $Na^+$ channels together with the absence of charged residues in trp1 and trp suggested that these proteins may form voltage independent ion channels. This was demonstrated recently by expression of the cDNAs for trp and trp1 in insect Sf9 cells using the baculovirus system. It was found that trp forms a $Ca^{2+}$ permeable cation channel which is activated by store depletion with thapsigargin [10] whereas trp1 forms a $Ca^{2+}$ permeable non-selective cation channel which is not only constitutively active when over-expressed in Sf9 cells but also can be up-regulated by receptor stimulation [11–13]. However, it was also noticed that neither trp nor trp1 mimicked the endogenous $Ca^{2+}$ influx channel of the St9 cells, suggesting the existence of at least one other channel in insects involved in $Ca^{2+}$ entry [10].

SUMMARY OF THE INVENTION

The present invention is based on our isolation of two trp proteins from human cells (Htrp1 and Htrp2) and the discovery that the trp proteins are responsible for and essential to the capacitative calcium ion entry (CCE) mechanism found in mammalian cells. Among other things, this discovery allows one to provide methods which control calcium ion levels in cells by regulating the expression of biologically active trp proteins. In addition to being a target for controlling calcium ion entry, the trp proteins may also be used in screening procedures for determining whether or not certain compounds should be considered candidates for regulating calcium ion levels in mammalian cells.

In accordance with the present invention, a method is provided for controlling capacitative calcium ion entry into a mammalian cell where the cell naturally expresses a transient receptor potential (trp) protein that is required for capacitative calcium ion entry into the cell. The method includes the step of treating the cell with a sufficient amount of a trp-control agent to either raise or lower the amount of biologically active trp protein associated with the cell to thereby control capacitative calcium ion entry into said cell.

As a feature of the present invention, the trp-control agent is a nucleotide sequence which codes for the expression of trp protein when said nucleotide sequence is introduced into said cell. The increase in expressed trp protein results in an increase in capacitative calcium entry into the cell. The trp-control agent may also be an anti-sense nucleotide sequence which is anti-sense to a nucleotide sequence which codes for the expression of trp protein. The anti-sense sequence can be used effectively to reduce the expression of trp protein and thereby reduces the influx of calcium ions into the cell. Inhibitors may also be used which bind to or otherwise inhibit the biological activity of the trp protein once it has been expressed by the cell.

As another feature of the present invention, methods are provided for screening compounds to determine their potential for use in controlling capacitative calcium ion entry into mammalian cells. The method involves providing a cell culture which expresses a transient receptor potential (trp) protein which is necessary for capacitative calcium ion entry into the cell. The cell expresses trp protein naturally in amounts which produces a naturally occurring level of biologically active trp protein associated with said cell. The cell culture is exposed to the compound of interest. A determination is then made to ascertain if the exposure of the cell culture to the compound produces an increase or decrease in the expression of the trp protein to thereby provide an indication of the compounds potential use in controlling capacitative calcium ion entry into mammalian cells.

The above discussed and many other features and attendant advantages of the present invention will become better understood by reference to the following detailed description.

DETAILED DESCRIPTION OF THE INVENTION

Figure 1:
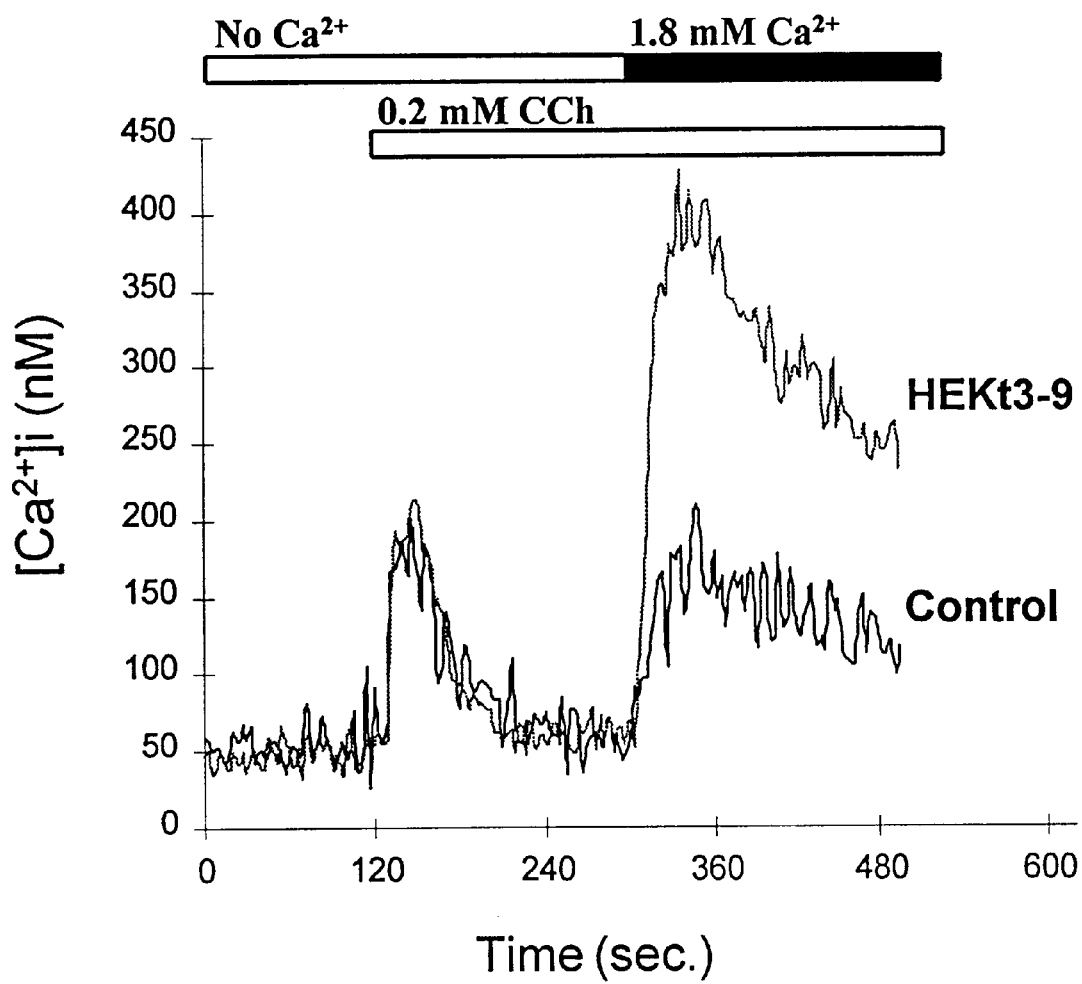
FIGS. 1–3 are graphical representations of the results of screening tests using carbachol (FIGS. 1 and 2) and maitotoxin (FIG. 3) as exemplary compounds being screened.

The various aspects of the present invention are based upon the isolation and characterization of two human trp proteins. The invention is further based upon the discovery that these proteins, as well as other mammalian cell trp proteins, are essential components of the calcium ion entry mechanism. The following portion of this detailed description sets forth the procedures used to isolate, identify, clone and functionally characterize the trp proteins.

Isolation and Identification of Htrp1

Expressed Sequence Tags (EST) are partial, "single-pass" cDNA sequences deposited in the Genbank database. Many of these sequences are homologous to proteins from other organisms and many of them may contain protein-coding regions that represent novel gene families [16]. We reasoned that such a cDNA sequence encoding a mammalian homologue for the trp gene might exist in the database. Therefore, we used the deduced amino acid sequence of the Drosophila trp as a query to search the Genbank database using 'tblastn', a program that allows comparison of a protein query sequence against a nucleotide sequence database dynamically translated in all reading frames. A human EST (EST05093) was found to encode an amino acid sequence that shares similarity with the Drosophila trp sequence from Glu33 to Asn80.

The 297 nucleotide sequence of this EST was determined from a cDNA clone isolated from a fetal human brain cDNA library and was deposited in GenBank by Adams et al. [16]. The deduced peptide sequence of EST05093 was then compared with the protein sequences of the Drosophila trp1 and a C elegans trp homologue (ZC21.2, Genbank accession # L16685). This revealed that the C-terminal region of the EST peptide is homologous to the N-terminal regions of all the trp-type proteins. We thus synthesized an oligonucleotide according to the 3' region of the EST05093 and used it as a probe to screen a human kidney cDNA library. From $1.5 \times 10^6$ recombinant phage, we isolated one positive clone, T23. An EcoRI digest of the purified λgt10 phage DNA produced three fragments. Among them, a 470 bp fragment hybridized to the oligonucleotide probe used for screening. The sequence of this fragment was determined and found to contain the complete sequence of EST05093. The sequences of the other two EcoRI fragments were found to contain open-reading frames which encode amino acid sequences homologous to the trp proteins down-stream from the region homologous to ETS05093. Thus, T23 was identified as a human trp homologue and has been named human trp-1 or Htrp-1 (SEQ. ID. NO. 1).

A 670 bp EcoRI fragment from T23 was then used as a probe to screen other human cDNA libraries, including a λZAP aorta, a λZAP cerebellum, a λgt10 heart and a specifically primed λgt10 library made from oligo-dT-purified HEK 293 cell mRNA. From all isolated cDNA clones, 13 were sequenced completely. These cDNA clones cover an mRNA of about 5.5 Kb, with an open-reading frame of 2379 bases. Comparison of overlapping DNA sequences of clones obtained from kidney, aorta, cerebellum, and heart showed only two silent substitutions of nucleotides which may arise because of polymorphism. Therefore, all the cDNA clones should be the product of the same gene locus.

The open reading frame of the Htrp-1 encodes a protein of 793 amino acids. A stop codon is present at 366 bases upstream from the first methionine in the same reading frame. The codon for the second methionine in this sequence matches better than the first methionine codon the sequence characteristics for translation initiation as specified by Kozak [17]. Therefore, the translated open reading frame may contain only 792 instead of 793 codons. A more detailed analysis of the cDNA clones indicated that the primary transcript of Htrp-1 gene may be spliced in alternative ways. Many of the cDNA clones do not contain a stretch of 102 base pairs which encodes amino acids 109 to 143. This gives rise to a shorter form of Htrp-1 with only 759 amino acids.

Searching the Genbank database using 'blastp' and the Htrp-1 protein sequence as a query, we found that only Drosophila trp, Drosophila trp1 and *C. elegans* trp have probability scores higher than 300. The remainder of the matched sequences had scores lower than 70. The Htrp-1 is about 37% identical or 62% similar to each of the other three known trp proteins. Sequence alignment of all four trp proteins shows conserved clusters of short amino acid sequences distributed throughout the entire length of the polypeptides, except that Htrp-1 and *C. elegans* trp have much shorter C-termini. As seen with Drosophila trp, Drosophila trp1 and *C. elegans* trp, hydropathy analysis of the Htrp-1 protein suggests 8 hydrophobic regions. These could correspond to transmembrane segments.

The evolutionary distances between each pair of the four trp proteins determined by the Kimura method [19] are shown in Table 1.

TABLE 1

EVOLUTIONARY DISTANCES OF THE trp PROTEINS

|  | Dtrp | Dtrp1 | Ctrp |
|---|---|---|---|
| Htrp-1 | 124 | 122 | 128 |
| Dtrp |  | 78 | 130 |
| Dtrp1 |  |  | 124 |

Evolutionary distances were determined using the Kimura protein distance analysis method. The non-conserved regions at the N— and C-termini were not included for calculation of the distances.

A Northern analysis using a fragment of Htrp-1 as a probe shows that a transcript of about 5.5 Kb is abundant in human heart, brain, ovary, and testis. Lower amounts of the transcript are also present in many other tissues including, kidney, lung, spleen, pancreas, thymus, skeletal and smooth muscle of the present invention. The Htrp-1 transcript is not detected in human liver mRNA by Northern blotting. However, a mouse trp-1 sequence which is 99% homologous to Htrp-1 is obtained from mouse liver mRNA by RT-PCR, indicating the presence of Htrp-1 in liver mRNA in low amounts.

The materials and methods used to isolate and identify the Htrp1 are as follows:

Isolation and Sequencing of cDNA Clones

We used a synthetic 45 nucleotide long oligonucleotide sequence, 5'-TTGAACATAAATTGCGTAGATGTGCTTGGGAGA-AATGCTGTTACC-3' (SEQ. ID. NO:3), labeled at the 5'-end with $^{32}$P by incubating with [γ-$^{32}$P]ATP in the presence of T4 polynucleotide kinase to screen a λgt10 human kidney cDNA library using standard protocols as described [14]. Hybridization was carried out in a shaking waterbath at 65° C. overnight. The filters were washed at 65° C. with 2×SSC/0.1% SDS (1×SSC is 150 mM NaCl/15 mM sodium citrate, pH 7.0). One positive clone was obtained from this library containing an insert of 1.5 Kb with multiple EcoRI sites. The EcoRI fragments were subcloned into plasmid Bluescript KS(+) and sequenced. One 0.67 Kb EcoRI fragment was later used as a probe for subsequent screening of other human cDNA libraries after labeling with [α-$^{32}$P] dCTP using the Klenow enzyme and random hexamers [15].

A primer specific library was constructed to facilitate the cloning of the N-terminal region of the Htrp-1 gene. PolyA RNA was prepared from 2.5×10$^8$ from human embryonic kidney cells, HEK 293, using an mRNA isolation kit from Collaborative Biomedical Products (Bedford, Mass. USA). Complementary DNA was synthesized, using a cDNA Synthesis module from Amersham, starting with 5 μg of the mRNA and a mixture of the following oligonucleotide primers: 5'-TCGCACGCCAGCAAGAAAAG-3' (SEQ. ID. NO:4), 5'-CGATGAGCAGCTAAAATGAC-3' (SEQ. ID. NO:5), and 5'-TGTCAGTCCAATTGTGAAAGA-3' (SEQ. ID. NO:6), each at the final concentration of 1.4 μM. A λgt10 library was constructed using Amersham cDNA cloning kits following manufacturer's protocols.

DNA inserts were sequenced by the dideoxynucleotide termination method using [α-$^{35}$S]dATP and Sequenase version 2.0 (United States Biochemical) as previously described [15]. The sequence was confirmed by sequencing both strands using double-stranded plasmids as templates and either universal primers or Htrp-1 specific synthetic oligonucleotides as primers. Other standard nucleic acid and bacteriological manipulations were performed as described [14].

Database Searches and Sequence Analysis

Protein and nucleic acid searches were performed using the BLAST network service of the National Center for Biotechnology Information via an e-mail server. DNA fragment assembly, restriction mapping, protein hydropathy analysis and alignment and all other sequence dependent analyses were performed using the Wisconsin Sequence Analysis Package from the Genetics Computer Group (GCG).

Northern Analysis

Human multiple tissue Northern blots (Clontech) were prehybridized in a Rapid-hyb buffer (Amersham) at 60° C. for 2 hours and then hybridized in the same buffer with $^{32}$P-labeled cDNA probe (4×10$^6$ cpm/ml) at 60° C. for 14 hours. After rinsing with 2×SSC/0.05% SDS, the filters were washed twice in the same solution and then twice in 0.2× SSC/0.1% SDS at 60° C. The filters were exposed to X-ray film at −70° C. with intensifying screens for desired periods of time. The probe for Htrp was made from the 0.67 Kb EcoRI fragment of the Htrp-1 cDNA and a control probe was a human cDNA for β-actin. Both probes were labeled by random prime labeling with [α-$^{32}$P]dCTP.

Isolation and Identification of Htrp3

The full length Htrp3 cDNA was cloned as follows: mRNA was prepared from human embryonic kidney cells (HEK 293 cells) [Zhu et al., 1995]. A library for rapid amplification of cDNA ends through amplification by the polymerase chain reaction (RACE-PCR) was prepared using 1 μg HEK mRNA, adaptors, reagents and protocols provided by Clontech in the Marathon cDNA Amplification kit. Specific oligonucleotide primers S1 (5'-TGA-CTTCCGTTGTGCTCAAATATGATCACAAATTCATAG-3') (SEQ. ID. NO:7), S2 (5'-ATGGAATATACAA-TGTAACTATGGTGGTCG-3') (SEQ. ID. NO:8), A1 (5'-GGACTAGGAACTAGACTGAAAGGTGGAGGTAAT-GTTTTTCCATCATCA-3')(SEQ. ID. NO:9), and A2 (5'-CGAGCAAACTTCCATTCTACATCACTGTC-3') (SEQ. ID. NO:10) were synthesized according to the sequence of EST R34716 from the GenBank dbEST database. Primary RACE-PCR amplifications were performed using AP1 (adaptor-ligated primer provided by the manufacturer) in combination with primer S1 for 3' amplification or AP1 with primer A1 for 5' amplification of Htrp3. Nested-PCR amplifications were performed using internal primers AP2 (Clontech) plus S2 for the 3' RACE or AP2 plus A2 for the 5' RACE. Polymerase chain reactions were carried out in a thermal cycle controller (MJ Research) using the Takara Ex Taq polymerase for 30 cycles each consisting of a denaturing step at 94° C. for 40 sec and an annealing plus extension step at 70° C. for 5 min. PCR products were extracted from agarose gel following electrophoresis and subcloned into a T/A cloning plasmid, pCRII (Invitrogen). Positive clones were identified using end-abeled oligonucleotides A1 and S1 for the 3' and 5' RACE, respectively, following a standard colony screening protocol [Sambrook et al. (14)]. DNA was sequenced by the dideoxy-chaintermination method of Sanger et al. (49) using double stranded DNA as template as described by Levy et al. (15). The sequence was confirmed by isolating overlapping partial cDNAs made directly from HEK 293 cell mRNA by RT-PCR with multiple sets of specific primers derived from the Htrp3 sequence. The nucleotide sequence of the Htrp3 cDNA has been deposited in GenBank (see below) and is set forth in SEQ. ID. NO. 2.

Partial cDNA fragments of murine trp homologues were cloned by reverse transcribing polyA$^+$ RNA from liver, brain and kidney and subjecting the transcripts to amplification by the polymerase chain reaction (RT-PCR). The primers used for amplification of reverse transcripts were: 5'-GCNGA(G/A)GGNCTCTT(T/C)GC (SEQ. ID. NO:11) (sense)/5'-CGNGC(G/A)AA(C/T)TGCA(A/G)(A/G)T (SEQ. ID. NO:12) (antisense) for Mtrp2(a); 5'-TGGGNCCN(C/T)TGCA(A/G)(A/G)T (SEQ. ID. NO:13) (sense)/5'-CGNGC(G/A)AA(C/T)TTCCA(C/T)TC (SEQ. ID. NO:14) (antisense) Mtrp1 and Mtrp2(b); 5'-ACCTCTCAGGCCTAAGGGAG (SEQ. ID. NO:15) (sense)/5'-CCTTCTGAAGTCTTCTCCTTCTGC (SEQ. ID. NO:16) (antisense) for Mtrp3; 5'-TCTGCAGATATCTCTGGGAAGGATGC (SEQ. ID. NO:17) (sense)/5'-AAGCTTTGTTCGAGCAAATTTCCATTC (SEQ. ID. NO:18) (antisense) for Mtrp4 and Mtrp5; and 5'-A(C/A)(G/A)CCNTT(C/T)ATGAA(G/A)TT (SEQ. ID. NO:19) (sense)/5'-CCACTCCACGTCCGCATCATCC (SEQ. ID. NO:20) (antisense) for Mtrp6.

The primers used for amplification of murine genomic DNA isolated from the 129Sv embryonic stem cell AB2.2 as described by *Rudolph* et al. (50) were: 5'-GGTTTAGCTATGGGGAAGAGC (SEQ. ID. NO:21) (sense)/5'-TTTCCA(T/C)TCTTTATCCTCATG (SEQ. ID. NO:22) (antisense) for Mtrp1; 5'-TGGACATGCCTCAGTTCCTGG (SEQ. ID. NO:23) (sense)/ 5'-TTTCCA(T/C)TCCACATCAGCATC (SEQ. ID. NO:24) (antisense) for Mtrp2; 5'-GGCTATGTTCTTTATGGGATAT (SEQ. ID. NO:25) (sense)/5'-CCATCATCAAAGTAGGAGAGCC (SEQ. ID. NO:26) (antisense) for Mtrp3; 5'-ATGTCAAAGCCCAGCACGAGT (SEQ. ID. NO:27) (sense)/5'-AAGCTTTGTTCGAGCAAAMCCATTC (SEQ. ID. NO:28) (antisense) for Mtrp4; 5'-ATGTGAAGGCCCGACATGAGT (SEQ. ID. NO:29) (sense)/5'-TTTCCATTCAATATCAGCATG (SEQ. ID. NO:30) (antisense) for Mtrp5; and 5'-ATCGGCTACGTTCTGTATGGTGTC (SEQ. ID. NO:31) (sense)/5'-GGAAAACCACAATTTGGCCCTTGC (SEQ. ID. NO:32) (antisense) for Mtrp6.

PolyA+ RNA was prepared from mouse tissues using an mRNA isolation kit from Collaborative Biomedical Products (Bedford, Mass., USA). The first strand cDNAs were synthesized using Moloney Murine Leukemia Virus Reverse Transcriptase (Gibco BRL) with either random hexamers or oligo-dT as primers following established protocols (14). The PCR reaction mixture was composed of the cDNA, 0.2 mM dNTP, 0.2 or 1 $\mu$M of each primer, 1.5 mM of $MgCl_2$, and 25 unit/ml of Taq polymerase (Perkin Elmer). PCR reactions using reverse transcripts were carried out in a Thermal Controller (MJ Research Inc.). For amplification of reverse transcripts the cycles were: 1 min at 94° C., 1 min at the annealing temperature listed next to the primers, and 1 min at 72° C. for 30 to 35 cycles. For genomic DNA (from 129Sv mouse embryonic stem cells), the cycles were 30 sec at 94° C., 60 sec at 55° C. and 3.5 min at 72° C., ending with 10 min at 72° C.

The PCR products were separated on a 1% agarose gel by electrophoresis. Appropriate DNA fragments were extracted with Qiagen Gel Extraction kit and subcloned into a TA cloning vector, pCRII (Invitrogen). These and all other cDNA fragments used in this work were sequenced as described above. The DNA sequences were confirmed by sequence analysis of produces obtained from at least one additional independent PCR reaction for each specific trp-related gene fragment.

Expression Plasmids

The Mtrp1 (470 bp), Mtrp2 (470 bp), Mtrp3 (1,200 bp), Mtrp4 (1,200 bp), Mtrp5 (450 bp), and Mtrp6 (270 bp) cDNA fragments obtained by RT-PCR were subcloned in negative orientation downstream of the CMV promoter of expression vector pGW1H (British Biotech Pharmaceuticals, Oxford, UK).

The full length cDNAs encoding the M5 muscarinic receptor (32), Htrp1 (29), Htrp3 and murine luteinizing hormone receptor, mLHR were subcloned downstream of the CMV promoter of the expression plasmid pcDNA3 (Invitrogen).

Transfecton of COS-M6 and Ltk⁻ Cells

COS-M6 cells were transfected by the DEAE-dextran/chloroquine shock method (14) as described (30) with changes. Sixteen hours prior to transfection, COS-M6 cells that had been kept subconfluent were plated at a density of $2\times10^5$ cells/well onto 25 mm glass coverslips placed at the bottom of the wells of 6-well plates. Cells in the individual wells were then transfected with 160 $\mu$l of transfection mixture (30) containing 0.1 $\mu$g pcDNA3 with the M5 receptor cDNA, a three fold molar excess of pcDNA3 vector carrying either the Htrp3, Htrp1 or mLHR cDNA to bring the final concentration of DNA to 4 $\mu$g/ml. Cell were used 40 to 48 hours after transfection.

Mouse fibroblast Ltk⁻ cells ($3\times10^6$ cells/100 mm dish) were transfected by the calcium phosphate/glycerol shock method with 5 $\mu$g each of the plasmids with the antisense cDNAs and 0.5 $\mu$g of the pcDNA3 carrying the M5 receptor. The control cells received only the M5 muscarinic receptor cDNA in pcDNA3. One day after transfection, the cells were trypsinized and diluted with Minimum Essential Medium—α medium containing 10% heat-inactivated fetal bovine serum, 50 units/ml penicillin, 50 $\mu$g/ml streptomycin, and 400 $\mu$g/ml G418 (GIBCO). Serial 1:4 dilutions of the cells were transferred into 96-well plates and G418 resistant clones were allowed to develop for two weeks in the G418-containing medium. Single colonies were then expanded and the cells used for Fura2 fluorescence measurement of muscarinic receptor induced $[Ca^{2+}]_i$ transients. Of 17 control cell lines, 5 responded to CCh, and increased $[Ca^{2+}]_i$ through the capacitative influx path by 96±5 nM (difference between $[Ca^{2+}]_i$ at time of $Ca^{2+}$ addition and $[Ca^{2+}]_i$ 30 sec later (average±SD, 20 cells each of 5 cell clones). Of thirty G418-resistant cell lines obtained from transfecting Ltk-cells with M5 receptor plus the six antisense trp cDNAs, 9 responded to carbachol.

All cells expressing the M5 receptor, identified by their response to carbachol (CCh), were assumed to express also the co-transfected cDNA (Htrp3 or Htrp1) or antisense cDNA fragments.

Measurement of Changes in Intracellular $Ca^{2+}$ ($[Ca^{2+}]_i$)

Intracellular $Ca^{2+}$ transients were measured in individual cells by fluorescence videomicroscopy using the Attofluor Digital Imaging and Photometry attachment of a Carl Zeiss Axiovert inverted microscope. Cells (COS-M6 or L) were grown on circular coverslips, rinsed and incubated with 5 $\mu$M Fura2/AM (Molecular Probes) in Hepes buffered saline (HPSS: 120 mM NaCl, 5.3 mM KCl, 0.8 mM $MgSO_4$, 1.8 mM $CaCl_2$, 11.1 mM glucose, 20 mM Hepes-Na, pH 7.4) at 37° C. for 30 min and then washed with HPSS twice at room temperature. The coverslips with the cells were then clamped into a circular open-bottom chamber and mounted onto the stage of the microscope. $[Ca^{2+}]_i$ in individual cells was monitored at room temperature exciting Fura2 alternatingly at 334 and 380 nm and recording emitted fluorescence at 520 nm. All reagents were diluted to their final concentrations in HPSS and applied to the cells by surface perfusion. The duration of exposure to each reagent mixture is indicated by the horizontal lines above the graphs depicting the changes in $[Ca^{2+}]_i$ as a function of time. The system allows data acquisition from up to 99 user-defined variably-sized regions of interest per field of view. Data from 15 to 30 individual cells were thus collected per experiment and experiments were repeated until data from sufficient cells were collected to generate an ensemble average that was calculated after transfer into Microsoft Excel 5.0. Data acquisition was typically at 1.2 to 1.5 sec intervals and lasted for 500–800 seconds.

For assessment of the rate at which $[Ca^{2+}]_i$ falls after an initial stimulation with agonist, t=0 is the time of agonist addition; for assessment of rate of influx of $Ca^{2+}$ into cells in which $Ca^{2+}$ stores had been depleted by agonist, t=0 is the time of $Ca^{2+}$ readdition. $t_{1/2}$/values were obtained by fitting the function $A=A°exp(-t \cdot ln2/t_{1/2})+B$ to the data points shown.

Membrane Potential Measurement

The resting membrane potential of transfected murine L cells was measured using the patch clamp technique. On-cell patches were obtained in the voltage clamp configuration. Before going to the whole cell configuration, the amplifier was switched to current clamp mode so that the resting membrane potential could be measured at the moment access was gained to the cell interior. The pipette solution was composed of the following (in mM): potassium gluconate 140, KCl 5, $CaCl_2$ 0.5, $MgCl_2$, EGTA 5, Hepes 5, ATP 5, pH 7.1. The bath solution was the same as that used for $[Ca^{2+}]_i$ measurements by digital videomicroscopy.

Functional Expression of Htrp1 and Htrp3

The demonstration that trp proteins are components of CCE requires that their activity be determined in intact cells and recognized in a background of existing agonist-stimulated $Ca^{2+}$ influx. Two complementing approaches were used. The first was to express full length trp cDNAs in a mammalian cell and test whether they would increase CCE. The second was to expand our knowledge on the molecular complexity of the mammalian trp gene family and test whether expression of partial cDNAs of several members of this family in antisense direction would interfere with CCE. We reasoned that if both conditions could be met, we would be justified in concluding that the trp having this activity is a component CCE, i.e., the capacitative $Ca^{2+}$ entry pathway.

The Htrp3 cDNA was transfected into COS-M6 cells together with a marker gene that would identify cells that had taken up DNA from non-transfected cells. The marker gene used was the $G_q$-coupled M5 muscarinic receptor (M5R) (31). This receptor stimulates phospholipase C (PLC) (31,32) and served as a trigger to activate CCE. Our initial experiments characterized $Ca^{2+}$ transients in COS-M6 cells transfected only with the M5 receptor. Stimulation of the PLC/IP3 pathway through the M5 receptor by addition of carbachol (CCh) caused an immediate fast rise in cytosolic $Ca^{2+}$ ($[Ca^{2+}]_i$) to a peak level that fell with an approximate $t_{1/2}$ of 30 sec to a plateau that was above the starting resting level. Maintenance of this plateau was dependent on both continuous $Ca^{2+}$ entry from the extracellular medium and on the continuous stimulation of the M5 receptor/G protein/PLC/IP3 pathway by the receptor agonist, as it was blocked upon addition of the receptor antagonist atropine. Although this was not assessed specifically in COS cells, we believe that the initial fast rise in $[Ca^{2+}]_i$ is due to IP3-stimulated release of $Ca^{2+}$ from intracellular stores (33). In agreement with this interpretation, the fast rise in $[Ca^{2+}]_i$ in response to CCh occurred also in the absence of extracellular $Ca^{2+}$ ($Ca^{2+}$-free medium plus 0.5 mM EGTA), but rather than falling to an above-basal plateau, fell to levels very close to basal. Addition of $Ca^{2+}$ to cells that had undergone the initial agonist-induced $[Ca^{2+}]_i$, increase in the absence of $Ca^{2+}$, then resulted in a rise in $[Ca^{2+}]_i$. This entry of $Ca^{2+}$ is a measure of agonist-activated CCE. Under these conditions, $Ca^{2+}$ influx was dependent on expression of the M5 receptor. Addition of $Ca^{2+}$ to cells kept for up to 10 minutes in $Ca^{2+}$-free medium in the absence of CCh also failed to show $Ca^{2+}$ influx. These features of agonist activated $Ca^{2+}$ transients have been shown previously for the M5 receptor expressed in stable form in murine L cells (32).

We next tested whether Htrp3 would affect M5 receptor induced capacitative $Ca^{2+}$ transients. We expected the putative trp-mediated $Ca^{2+}$ entry to reduce the rate at which $[Ca^{2+}]_i$ falls after the initial effect of IP3, and possibly to increase the steady state (plateau) level of $[Ca^{2+}]_i$. We expected also that cells stimulated in the absence of extracellular $Ca^{2+}$ would show, upon $Ca^{2+}$ re-addition, a faster $Ca^{2+}$ influx leading to a higher $[Ca^{2+}]_i$.

Cells that had been transfected with expression vectors carrying the M5 receptor and, as appropriate, either the newly cloned Htrp3 cDNA or the previously cloned Htrp1 cDNA (29), were grown on coverslips, loaded with the florescent $Ca^{2+}$ indicator dye Fura2 and tested for a response to CCh 40–48 hours after transfection. For purpose of analysis the cells that responded to carbachol were assumed to be expressing not only the receptor but also the co-transfected trp cDNA. Changes in $[Ca^{2+}]_i$ as a function of time were recorded from individual cells, averaged and fitted by a first order decay function plus an offset.

The decay of the carbachol/IP3-induced peak $[Ca^{2+}]_i$ in the presence of extracellular $Ca^{2+}$ was well fit by the first order decay function, and the rate of return was slower in cells transfected with Htrp3 than in cells transfected with the M5R only: $t_{1/2}=27\pm3$ sec for cells with M5R only (mean±SEM; number of individual M5R positive cells analyzed (n)=81) vs. 37±4 sec for cells transfected with M5R plus Htrp3 (n=81; p<0.01). In contrast, the decay in cells transfected with M5R plus Htrp1 ($t_{1/2}=24\pm3$ sec, n=104) was not significantly different from that seen in cells transfected with M5R alone. Furthermore, the fit required an offset or plateau of $[Ca^{2+}]_i$ that was 2.2 to 2.5 times that of the $[Ca^{2+}]_i$ at the time of CCh addition. This plateau showed a small, but significant difference between control and Htrp3 transfected cells (88 nM (95% confidence limits: 77–101 nM) vs. 117 nM (95% confidence limits: 105–130 nM). The plateau derived from the fit for Htrp1-transfected cells did not differ significantly from that of either control or Htrp3-transfected cells.

The effect of readdition of $Ca^{2+}$ to cells that had been stimulated with CCh in the absence of $Ca^{2+}$ showed that $Ca^{2+}$ influx into cells transfected with Htrp3 was faster and lasted longer than in control cells causing $[Ca^{2+}]_i$ to increase to levels that were 200% to 230% above those seen in cells transfected without Htrp3. It is noteworthy that while co-expression of Htrp1 had no measurable effect on the rate of decay of the IP3-induced peak $[Ca^{2+}]_i$, it did cause a significant increase in $Ca^{2+}$ influx when measured by the $Ca^{2+}$ readdition protocol. The magnitude of the effect of Htrp1, a maximum of 75% over control, was smaller than that of Htrp3. Thus, the $Ca^{2+}$ readdition protocol is a more sensitive way of measuring changes in $Ca^{2+}$ influx than assessing changes in the kinetics of the IP3-induced $[Ca^{2+}]_i$ transient or changes in plateau $[Ca^{2+}]_i$ as seen in the continuous presence of extracellular $Ca^{2+}$.

Various aspects of the Htrp3-induced $Ca^{2+}$ influx are set forth below. The first was to determine that increased $Ca^{2+}$ influx was not merely a non-specific leak that developed in response to protein overexpression. This was addressed by testing whether $Ca^{2+}$ influx in the presence of Htrp3 could be inhibited by lanthanum and nickel, which both inhibit capacitative $Ca^{2+}$ influx (34,35). For lanthanum, the Htrp3-stimulated $Ca^{2+}$ influx is fully inhibited by 1 mM $La^{3+}$, as is the CCE endogenous to COS cells. Htrp3-mediated $Ca^{2+}$ influx differed from agonist-stimulated COS cell CCE in that it was significantly less sensitive to low concentrations of $La^{3+}$. At 250 $\mu$M, endogenous $Ca^{2+}$ influx was 80–90% blocked while the difference due to Htrp3 influx was blocked only 30–40%. In another set of examples we found that endogenous CCh-stimulated CCE was blocked >90% by 2 mM $Ni^{2+}$, while CCh-stimulated influx due to Htrp3 was inhibited by only 20%; 10 mM $Ni^{2+}$ blocked $Ca^{2+}$ influx in Htrp3 cells 85%. Although it still needs to be determined whether part of the endogenous COS cell CCE is Htrp3-like, the above results demonstrate that $Ca^{2+}$ entry stimulated by expression of Htrp3 is not due to appearance of a non-specific leak.

We also tested whether $Ca^{2+}$ influx in Htrp3 transfected cells allowed passage of $Mn^{2+}$. Some forms of CCE channels allow passage of $Mn^{2+}$ while others do not (36,37). We thus depleted internal stores in $Ca^{2+}$ free medium by addition of CCh, allowed $[Ca^{2+}]_i$ to return to baseline levels (range: 40 and 60 nM) and then added 25 $\mu$M $MnCl_2$ so as to monitor $Mn^{2+}$ entry by its effect to quench the fluorescence signal of Fura2 excited at 380 nm. In Htrp3-transfected cells the Fura2 signal was quenched at a rate of 0.14%/sec, which was 3-times faster than quenching observed in control cells (0.05%/sec, data not shown). These finding indicated that in control cells as well as in Htrp3-transfected cells, $Ca^{2+}$ enters through channels that allow passage of $Ca^{2+}$ and $Mn^{2+}$.

We tested whether the Htrp3-induced influx is regulated by store depletion in the absence of agonist. Cells were placed into $Ca^{2+}$ free medium plus 500 nM TG to inhibit internal Ca pumps and thus promote agonist-independent store depletion. $Ca^{2+}$ (1.8 mM) was then added to measure $Ca^{2+}$ influx. The store depletion-activated increase in $[Ca^{2+}]_i$ was larger in Htrp3-transfected cells than in control cells indicating that Htrp3 dependent $Ca^{2+}$ influx can be activated by store depletion independent of prior activation of the G-protein/PLC/IP3 pathway. As in control experiments with agonist-stimulated $Ca^{2+}$ entry, TG-stimulated $Ca^{2+}$ entry was also blocked >80% by 250 $\mu$M $La^{3+}$ while $Ca^{2+}$ entry into Htrp3 transfected cells showed a significant residual $Ca^{2+}$ entry confirming stimulation of a distinct type of $Ca^{2+}$ entry pathway. We noted that the increase in TG-stimulated $Ca^{2+}$ influx due to expression of Htrp3 is of a more transient nature than the endogenous TG-stimulated $Ca^{2+}$ influx. The above tests demonstrate that Htrp3- and Htrp1-mediated CCE is subject to regulation by store depletion and does not require simultaneous stimulation by an agonist, and also, that there are differences with respect to the endogenous COS cell CCE. It appears also that Htrp3-mediated $Ca^{2+}$ influx may be more sensitive to agonist-promoted store depletion than thapsigargin-mediated store depletion.

The above description shows that mammalian homologues of insect channels that were expressed in mammalian cells could permeate $Ca^{2+}$ in response to a manipulation that activates endogenous CCE. These results did not rule out the possibility that while expression of these homologues mimicked CCE, they were not the type of molecules that naturally fulfilled this function in mammalian cells. We thus investigated the molecular diversity of mammalian trp genes, cloned partial cDNA fragments and expressed these in the antisense direction in a mammalian cell line (murine L cells) to determine whether they would interfere with natural CCE.

Molecular Diversity of the trp Family.

We found by Northern analysis that Htrp1 is expressed human tissues with higher amounts in ovary, testis, heart and brain. Htrp1 is not expressed in liver. Since agonist-stimulated calcium influx is readily demonstrable in liver (38,39), this suggested strongly that if trp-related proteins participated in or were to be responsible for this type of $Ca^{2+}$ influx, the mRNA encoding the particular trp carrying out this function in liver should be represented in liver RNA. Using mouse liver polyA$^+$ RNA as template and degenerate sets of primers based on the amino acids known to be conserved in Drosophila trp (Dtrp), Drosophila trp-like (Dtrp1), *Caenorhabditis elegans* trp (Cetrp) and Htrp1, we amplified and cloned a PCR fragment of 405 bp that had a continuous open reading frame of 135 codons encoding an amino acid sequence very similar to that encoded in the human pseudogene-derived EST T67673 (ΨHtrp2), with two exceptions: 1, that alignment of the murine sequence with other trp sequences did not require introduction of a 31 amino acid gap and 2. that where EST T67673 has a Stop codon we found the CGA codon for Arg.

Using a second set of sense and antisense primers, we amplified and cloned another PCR fragment which, except for beginning 93 nt downstream from the first, had the same nucleotide sequence as the first and hence encoded the same murine trp-homologue, Mtrp2. Using mouse brain polyA$^+$ RNA as template and other mixtures of degenerate oligonucleotides we identified cDNA fragments that potentially encoded five additional murine trinelated proteins. Published data (40, 41) and a query of dbEST had predicted that including the human pseudogene we should have found only three additional murine trp-related gene products. A comparison of the predicted amino acid sequences of the cDNA fragments obtained by RT-PCR to known trprelated sequences showed that we had obtained in addition to Mtrp1, Mtrp2 and Mtrp3, the murine equivalents of their human counterparts, Mtrp4, a murine sequence described by (40), and two new sequences, Mtrp5 and Mtrp6. Compared to Mtrp5, Mtrp1, -2, -3, -4 and -6 differ at the nucleotide level by 53, 46, 40, 22 and 39 percent, respectively. Ignoring gaps, the same comparison at the amino acid level shows Mtrp1, -2, -3, -4 and -6 to differ from Mtrp5 in this region of the proteins by 57, 49, 45, 7, and 56% percent, respectively.

Murine genomic DNA was tested for the presence of six distinct trp genes using a PCR approach. All the trp cDNA sequences reported here lie immediately upstream of a highly conserved EWKFAR motif. Using as 3' PCR primers, antisense oligonucleotides based on this motif, and as 5' PCR primers, exact sense oligonucleotides specific for each of the six trp transcripts, it was possible to amplify genomic fragments from four of the six murine trp genes. The length of these fragments exceeded by 600 bp to 2.8 kb that of the 180 bp product predicted if there would have been no intron between the primers, indicating that the primers spanned introns that varied in length in the separate genes. The PCR fragments were cloned and their identity was confirmed by sequencing the intron-exon boundaries. One explanation for our failure to amplify a fragment of the Mtrp1 and Mtrp5 genes is that in these genes the introns are too large to amplify under the conditions used. Another explanation could be that for these genes the EWKFAR motif on which the 3' primers were based is not absolutely conserved in these genes—in the *C. elegans* trp it is EKWFHR—which could make our primers ineffective in the PCR reaction. Absence of an intron between the primers would have yielded a 180 bp fragment, which was not obtained. The identification of distinct genomic fragments for four of the trp sequences found by RT-PCR provides independent confirmation for the existence of four of the six trp genes inferred from by analyzing the RT-PCR products. The fact that these genes have conserved intron/exon boundaries is further proof of the evolutionary relatedness of the sequences identified by RT-PCR.

Inhibition of Endogenous CCE by trp Antisense Sequences.

The results presented in the preceding paragraphs increased the number of possible trprelated proteins that could be involved in agonist- and store-operated CCE to six. The murine trp-related sequences were cloned in their antisense direction downstream of the CMV promoter of the eukaryotic expression vector pGW1H and transfected together with the M5 receptor (in pcDNA3) into murine L cells. Cells transformed by pcDNA3 DNA were isolated by growing in G418-containing medium. pcDNA3, but not pGW1H, carries the neomycin resistance gene. Transfection of L cells with human genomic DNA has shown that these cells are able to incorporate in stable form as much as 1.5 million base pairs (42). On the basis of this we assumed that cells selected for transformation by the pcDNA3 vector were likely to have incorporated also the pGW1H vectors with the six antisense trp sequences and hence to be co-expressing the M5 receptor and the anti-trp sequences. Cells from the isolated cell clones that were positive for M5 receptor expression as seen by their ability to respond to CCh with an IP3-induced rise and fall in $[Ca^{2+}]_i$, were then tested for their ability to mount a capacitative $Ca^{2+}$ influx response. In six of the nine M5 receptor positive cell lines that been transfected with both the M5 receptor and antisense cDNA fragments, the expression of antisense sequences fully prevented activation of CCE. As determined for cells from two cell lines transfected with antisense cDNAs and showing no agonist-stimulated CCE, the loss of CCE was not due to a collapse their resting membrane potentials. Thus, the resting membrane potentials (mean±SEM) of cells from clones a6.19 and a6.5, which had their CCE responses suppressed, were −30±4 mV (n=8) and −35±4 mV (n=8), respectively; and those of cells from clones c.1 and c.4, which expressed the M5 receptor alone and showed agonist-activated CCE, were −27±2 mV (n=8) and −34±4 mV (n=8), respectively. None of these membrane potentials differed significantly from the other (p>0.01). This indicated that loss of CCE was not a non-specific effect of the antisense sequences causing a collapse of the membrane potential. These examples further demonstrate that one or more of the mammalian trp homologues Htrp1 and Htrp3 are components of the CCE pathway, and vice versa that CCE is totally dependent on one or more trp-related gene products.

Primary Structure, Tissue Expression and Model of Topology of Htrp3.

Northern analysis detected an Htrp3 mRNA of ca. 4 Kb predominantly in brain, and at much lower levels also in ovary, colon, small intestine, lung, prostate, placenta and testis. A larger size mRNA present at a lower level in brain, could be composed of incompletely processed mRNA or alternatively spliced products.

A Kyte-Doolittle analysis revealed a core of eight hydrophobic regions of which six could encode transmembrane segments based on degree of hydrophobicity and length ($\geq 16$ amino acids). This core is 320 amino acids long and is delimited, in analogy to other ion channels, by putative cytosolic N- and C-termini that are 350 and 200 amino acids long, respectively.

The above results show that Htrp3 is a protein that enhances CCE in COS cells and that Htrp1 show a similar activity. The activity of these gene products was best observed when CCE was measured following agonist-stimulated depletion of intracellular stores in $Ca^{2+}$-free medium. This protocol is similar to that used by Petersen et al. (40) showing that expression of Drosophila trp in a vertebrate cell, the Xenopus oocyte, causes an increase in capacitative $Ca^{2+}$ influx of 66% in excess of the oocyte's endogenous CCE. The activities of Htrp1 and Htrp3, increasing $Ca^{2+}$ entry into COS cells by 75% and 230%, respectively, compare favorably to that of the insect channel.

In accordance with the present invention, the $Ca^{2+}$ influx due to Htrp3 was less sensitive to inhibition by $La^{3+}$ and $Ni^{2+}$ than $Ca^{2+}$ entry through the endogenous COS cell CCE channel(s). The CCE channel formed in Htrp3-expressing cells was found to permeate $Ca^{2+}$ and $Mn^{2+}$. Several reports during the last years have emphasized that hormones, growth factors and other cellular activators stimulate more than one $Ca^{2+}$ influx pathway (44,38,44a), and expression of the Drosophila trp and trp-like in Sf9 cells showed formation of two different type of channels. One is highly selective for $Ca^{2+}$ (trp) and activated upon TG-induced store depletion. The other, trp-like, shows no-selectivity for $Ca^{2+}$, is insensitive to store depletion, permeates mono-and divalent cations alike, is activated by IP3 and has a tendency for spontaneous agonist-independent activation (45,46,47,48). It is not known whether CCE channels with properties of insect trp and trp-like exist in vertebrate cells. The existence of a family of mammalian trp proteins described here, of which two members (Htrp1 and Htrp3) have the ability to increase $Ca^{2+}$ influx, and the effect of anti-trp sequences suppressing CCE in a fibroblast cell line, provide a formal link between the activity of Htrp3/Htrp1 and CCE.

As is apparent from the preceding description, mammalian trp proteins are a required component of capacitative calcium ion entry into mammalian cells. Accordingly, control of the amount of active trp protein in a cell provides a way to control the calcium ion level of the cell. Methods for controlling the amount of active protein expressed by a cell are well-known. For example the cells can be treated with nucleotides which are anti-sense to the gene which expresses the protein. This type of treatment prevents expression of the trp protein. Anti-sense treatment protocols are used when it is desired to reduce trp protein present in the cell and thereby reduce calcium ion entry. The nucleotide sequences may also be introduced into the cell in order to increase the expression of trp proteins and thereby increase calcium ion entry. These two procedures allow one to control calcium ion levels in the cell by either increasing or decreasing the level of trp protein expressed by the cell.

In addition to controlling trp protein expression, calcium ion entry can be controlled by treating the cell with an inhibitory agent which binds to or otherwise denatures the trp protein. Suitable types of inhibitory agents include imidazole derivatives such as SKF 96365, econazole, micozole, clotrimazole, and calmidazolium [Merrit et al. (52); Daly et al. (53)] plant alkaloids such as tetrandine and hernandezine (Low et al., 1996). The activity of trp may also be regulated by cellular substances known to affect CCE. Such substances include an unidentified diffusible messenger (CIF), inositol phosphates (IP3 and IP4), cyclic GMP, or by covalent modification by enzymes such as protein kinases, protein phosphatases, small GTPases and cytochrome P450. It has been suggested that maitotoxin may stimulate CCE channels [Worley et al. (54)].

Monoclonal antibodies may also be used as inhibitory agents. Suitable monoclonal and poyclonal antibodies could be obtained by standard techniques using purified GSTfusion proteins as antigens, which are also made by standard procedures and where the fusion aspect of the complex is a portion of the ectodomain of the trp protein. For Htrp3 this could be any stretch between amino acid 350 and 650. It is anticipated that such antibodies could modulate the CCE and be of therapeutic use.

Treatment of the mammalian cells with sense and anti-sense trp nucleotides and/or trp inhibitory agents can be accomplished in accordance with any of the known procedures for treating cells to control the production of a selected protein. The various dosages and amounts of selected agents which are required to achieve desired levels of calcium ion entry can be established by routine experimentation.

Examples of treatment protocols in accordance with the present invention involving the use of anti-sense nucleotides to reduce calcium ion levels are as follows:

Cellular Trp levels in cells can be regulated by introduction of antisense sequences by inserting partial or complete trp cDNAs in the antisense direction into viral expression vectors based on retroviruses or adenoviruses using protocols that are being applied for purposes of gene therapy as summarized in Chapter 5: *Gene Based Therapy* of Goodman and Gilman's Ninth Edition of *The Pharmacological Basis of Therapeutics* McGraw-Hill, pp. 77–101 (1996). Alternatively, oligonucleotides complementary to the coding region of trp molecules can be administered in to humans in pharmaceutical formulations such as aerosols or creams, if epithelia of the airways or cells in the dermis and epidermis are to be targeted. The same technique can be used to suppress trp expression in cultured cells in vitro.

Examples of treatment protocols in accordance with the present invention involving the use of trp control agents to control calcium ion levels are as follows:

inhibition of airway smooth muscle CCE to treat asthma
inhibition of vascular endothelial CCE to treat hypertension
stimulation of pancreatic β-cell CCE to stimulate insulin secretion in type II (non-insulin-dependent) diabetes
inhibition of osteoclast CCE to prevent osteoporosis
stimulation of osteoblast CCE to promote bone formation
inhibition of platelet CCE as an antithrombotic therapy
gene therapy of primary immunodeficiencies if they are due to mutations in trp genes (see references 55 and 56).

The dosage levels and treatment regimens for all of the above-mentioned uses for the present invention can be established using routine experimentation.

The discovery of the importance of Htrp protein in the control of calcium ion entry into the cell also provides a basis in accordance with the present invention to screen a large number of compounds to determine if they may be useful in controlling cellular calcium ion levels. In its simplest form, the screening method involves exposing the cell to a potential drug or other compound and determining if the level of trp protein is reduced. If the compound is effective in reducing trp protein levels, then it is considered a good candidate for use in reducing calcium ion entry into the cell.

The type of compounds which can be screened according to this aspect of the present invention are unlimited. The screening procedures which may be used to test compounds for their ability to inhibit trp protein are well-known to those skilled in the art. The same screening procedures which have been used to screen compounds for inhibitory properties with respect to other proteins and enzymes expressed by cells may be used. An exemplary screening protocol is set forth as follows.

Figure 2:
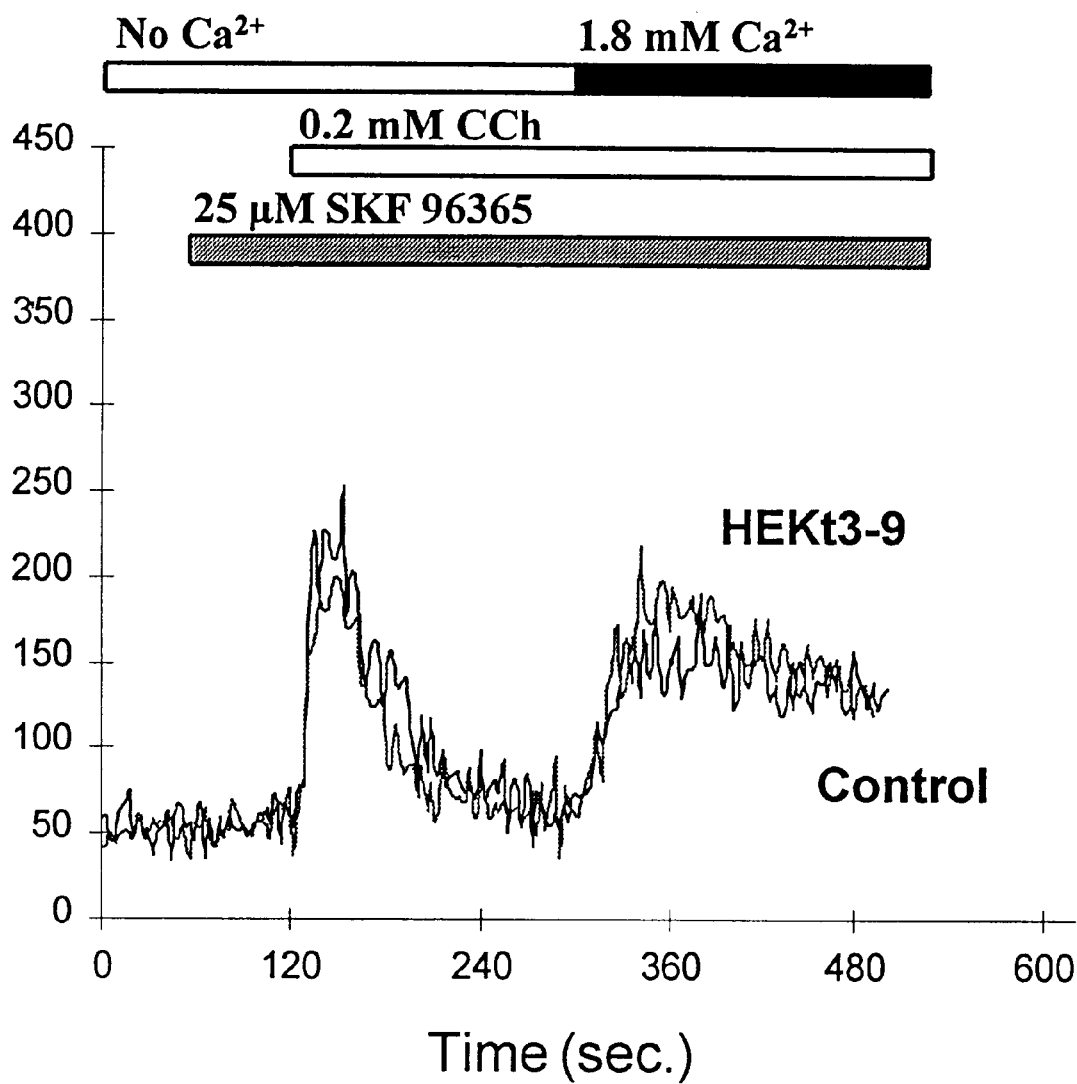
Figure 3:
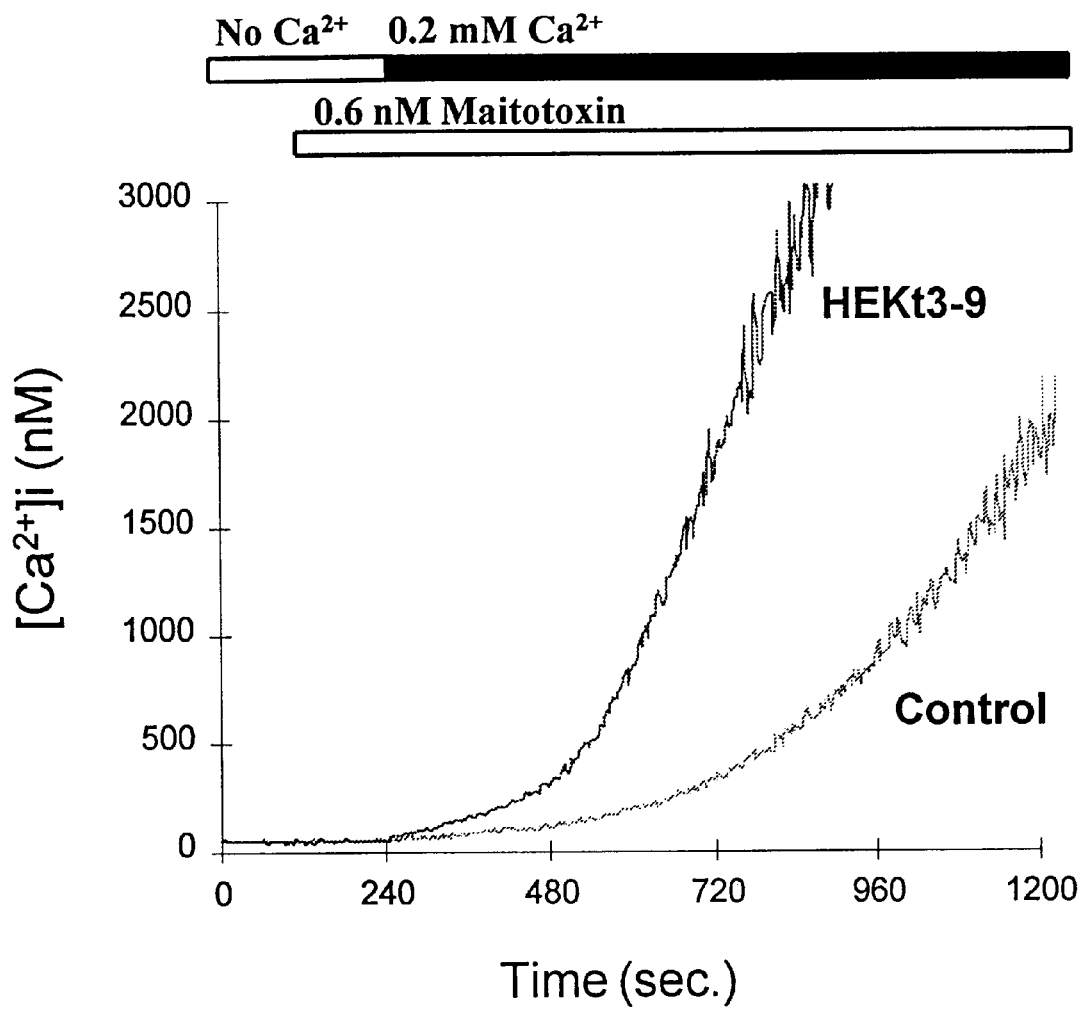

Trp proteins can be expressed in cells by standard recombinant means such as described in Innamoratti et al. (57), Gudermann et al. (58), Zhu et al. (59) and $Ca^{2+}$ influx monitored in single cells as described in Zhu et al. (30) or in a population of cells as described in Liao et al. (32). By doing this in the absence and presence of test compounds of which the effect on trp-mediated CCE can then be determined. An example is shown below (FIGS. 1 and 2) where human embryonic kidney cells (HEK-293 cells) expressing Htrp3 in stable form (HEKt3–9) are stimulated with carbachol and CCE is measured upon readdition of $Ca^{2+}$ to the extracellular medium. In the example, 25 μM SKF 96365 blocks selectively CCE due to Htrp3. It should be noted that CCE endogenous to the HEK 293 cell (control), presumably mediated by trp's other than Htrp3 is much less sensitive to this concentration of SKF 96365. Not only agents that block calcium entry due to trp expression but also agents that stimulate calcium entry due to trp can be monitored in this way. The second example, FIG. 3, below shows maitotoxin-stimulated $Ca^{2+}$ influx into HEK 293 cells that is several fold larger in cells expressing Htrp3 than in control cells.

In the above examples, cell were suspended in extracellular solution at a concentration of $20 \times 10^6$ cells/ml, loaded with Fura2AM (5 μM, 30 min), washed with solution nominally free of calcium, twice, and suspended at $2 \times 10^6$ cells/ml. Intracellular $Ca^{2+}$ concentrations were then monitored as described in Liao et al (32). Times and concentrations of additions are depicted by the bars in the Figures. Control cells were HEK 293 cells expressing an unrelated protein. For further details see references 32 and 30. Note in FIG. 1 that expression of Htrp3 in HEKt3–9 cells potentiates carbachol (CCh)-stimulated CCE and that the "extra-CCE" due to Htrp3 expression is blocked by 25 μM SKF 96365 in FIG. 2.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

BIBLIOGRAPHY

1. Berridge, M. J. (1993) *Nature* 361, 315–325.
2. Putney J. W. Jr. and Bird, G. S. (1993) *Endocrine Rev.* 14, 610–631.
3. Fasolato, C., Innocenti, B., and Pozzan, T. (1994) *TIPS* 15, 77–83.
4. Clapham, D. E. (1995) *Cell* 80, 259–268.
5. Kass, G. E. N., Chow, S. C., Gahm, A., Webb, D.-L., Berggren, P.-O., Liopis, J., Orrenius, S. (1994) *Biochim. Biophys. Acta* 1223, 226–233.
6. Hardie, R. C. and Minke, B. (1993) *TINS* 16, 371–376.
7. Montell, C. and Rubin, G. M. (1989) *Neuron* 2, 1313–1323.
8. Wong, F., Schaefer, E. L., Roop, B. C., LaMendola, J. N., Johnson-Seaton, D., and Shao, D. (1989) *Neuron* 3, 81–94.
9. Phillips, A. M., Bull, A., and Kelly, L. E. (1992) *Neuron* 8, 631–642.
10. Vaca, L., Sinkins, W. G., Hu, Y., Kunze, D. L., and Schilling, W. P. (1994) *Am. J. Physiol.* 267, C1501–C1505.
11. Hu, Y., Vaca, L., Zhu, X., Birnbaumer, L., Kunze, D. L., and Schilling, W. P. (1994) *Biochem. Biophys. Res. Commun.* 201, 1050–1056.
12. Hu, Y. and Schilling, W. P. (1995) *Biochem. J.* 305, 605–611.

13. Harteneck, C., Obukhov, A. G., Zobel, A., Kalkbrenner, F., and Schultz, G. (1995) *FEBS Letters* 358, 297–300.
14. Sambrook, J., Fritsch, E. F., and Maniatis, T. (1989) *Molecular Cloning: A Laboratory Manual* (Cold Spring Harbor Lab., Cold Spring Harbor, N.Y.) 2nd Ed.
15. Levy, F. O., Gudermann, T., Perez-Reyes, E., Birnbaumer, M., Kaumann, A. J., and Birnbaumer, L. (1992) *J. Biol. Chem.* 267, 7553–7562.
16. Adams, M. D., Kerlavage, A. R., Fields, C., and Venter, J. C. (1993) *Nature Genetics* 4, 256–267.
17. Kozak, M. (1991) *J. Cell Biol.* 115, 887–903.
18. Kyte, J. and Doolittle, R. F. (1982) *J. Mole. Biol.* 157,105–132.
19. Kimura, M. (1983) *The Neutral Theory of Molecular Evolution*, Cambridge University Press, Cambridge.
20. Hardie, R. C. and Minke, B. (1992) *Neuron* 8, 643–651.
21. Schneider, T., Wei, X., Olcese, R., Costantin, J. L., Neely, A., Palade, P., Perez-Reyes, E., Qin, N., Zhou, J., Crawford, G. D., and Birnbaumer, L. (1994) *Receptors and Channels* 2; 255–270.
22. Baringa, M. (1995) *Science* 267, 177–178.
23. Hoth, M. and Penner, R. (1992). Depletion of intracellular calcium stores activates a calcium current in mast cells. Nature 355, 353–356.
24. Hoth, M. and Penner, R. (1993). Calcium release-activated calcium current in rat mast cells. J. Physiol. 465, 359–386.
25. Zweifach, A. and Lewis, R. S. (1995a). Rapid inactivation of depletion-activated calcium current ($I_{CRAC}$) due to local calcium feedback. J. Gen. Physiol. 105, 209–226.
26. Zweifach, A. and Lewis, R. S. (1995b). Slow calcium-dependent inactivation of depletion-activated calcium current. Store-dependent and -independent mechanisms. J. Biol. Chem. 270, 14445–14451.
27. Putney, J. W., Jr. (1986a). A model for receptor-regulated calcium entry. Cell Calcium 7, 1–12.
28. Putney, J. W., Jr. (1990). Capacitative calcium entry revisited. Cell Calcium 11, 611–624.
29. Zhu, X., Chu, P. B., Peyton, M., and Birnbaumer, L. (1995). Molecular cloning of a widely expressed human homologue for the Drosophila trp gene. FEBS Lett. 373, 193–198.
30. Zhu et al. (1996) trp, A Novel Mammalian Gene Family Essential For Agonist-Activated Capacitative $Ca^{2+}$ Entry, *Cell*, Vol. 85, 661–671.
31. Liao, C.-F., Themmen, A. P. N., Joho, R., Barberis, C., Birnbaumer, M., and Birnbaumer, L. (1989). Molecular cloning and expression of a fifth muscarinic acetylcholine receptor (M5-mAChR). J. Biol. Chem. 264, 7328–7337.
32. Liao, C.-F., Schilling, W. P., Birnbaumer, M., and Birnbaumer, L. (1990). Cellular responses to stimulation of the M5 muscarinic acetylcholine receptor as seen in murine L cells. J. Biol. Chem. 265, 11273–11284.
33. Streb, H., Irvine, R. F., Berridge, M. J., and Schulz, I. (1983). Release of $Ca^{2+}$ from a nonmitochondrial intracellular store in pancreatic acinar cells by inositol-1,4,5-trisphosphate. Nature 306, 67–69.
34. Pandol, S. J., Schooffield, M. S., Fimmel, C. J., and Muallem, S. (1987). The agonist-sensitive calcium pool in the pancreatic acinar cell. Activation of plasma membrane $Ca^{2+}$ influx mechanism. J. Biol. Chem. 262, 16963–16968.
35. Kwan, C. Y., Takemura, H., Obie, J. F., Thastrup, O., and Putney, J. W. Jr.,
(1990). Effects of MeCh, thapsigargin, and La3+ on plasmalemmal and intracellular Ca2+ transport in lacrimal acinar cells. Am. J. Physiol. 258, C1006–C1015.
36. Fasolato, C., Innocenti, B., and Pozzan, T. (1994). Receptor-activated $Ca^{2+}$ influx: how many mechanisms for how many channels? Trends Pharmac. Sci. 15, 77–83.
37. Clapham, D. E. (1995b). Intracellular calcium: replenishing the stores. Nature 375, 634–635.
38. Kass, G. E. N., Chow, S. C., Gahm, A., Webb, D.-L., Berggren, P.-O., Llopis, J., and Orrenius, S., (1993). Two separate plasma membrane $Ca^{2+}$ carriers participate in receptor-mediated $Ca^{2+}$ influx in rat hepatocytes. Biochim. Biophys. Acta 1223, 226–233.
39. Berven, L. A. Hughes, B. P. and Barritt, G. J. (1994). A slowly ADP-ribosylated pertussis toxin-sensitive GTP-binding regulatory protein is required for vasopressin-stimulated $Ca^{2+}$ inflow in hepathocytes. Biochem. J. 299, 399–407.
40. Petersen, C. C. H., Berridge, M. J., Borgese, M. F., and Bennett, D. L. (1995). Putative capacitative calcium entry channels: expression of Drosophila trp and evidence for the existence of vertebrate homologues. Biochem. J. 311, 41–44.
41. Wes, P. D., Chevesich, J., Jeromin, A, Rosenberg, C., Stetten, G., and Montell, C. (1995). TRPC1, a human homolog of a Drosophila store-operated channel. Proc. Natl. Acad. Sci. USA 92, 9652–9659.
42. Kuhn, L. C., McClelland, A., and Ruddle, F. H. (1984). Gene transfer, expression, and molecular cloning of the human transferrin receptor gene. Cell 37, 95–103.
43. Phillips, A. M., Bull, A. and Kelly, L. E. (1992). Identification of a Drosophila gene encoding a calmodulin-binding protein with homology to the trp phototransduction gene. Neuron 8, 631–642.
44. Clementi, E., Scheer, H., Zacchetti, D., Fasolato, C., Pozzan, T., and Meldolesi, J. (1992). Receptor activated $Ca^{2+}$ influx. Two independently regulated mechanisms of influx stimulation coexist in neurosecretory PC12 cells. J. Biol. Chem. 267, 2164–2172.
44A. Montero, M., Garcia-Sancho, J., and Alvarez, J. (1994). Activation by chemotactic peptide of a receptor-operated $Ca^{2+}$ entry pathway in differentiated HL60 cells. J. Biol. Chem. 269, 29451–29456.
45. Vaca, L., Sinkins, W. G., Hu, Y., Kunze, D., Schilling, W. P. (1994). Activation of recombinant trp by thapsigargin in Sf9 insect cells. Am. J. Physiol. 267, C1501–C1505.
46. Dong, Y. Kunze, D., Vaca, L., and Schilling, W. P. (1995). Ins(1,4,5)$P_3$ activates Drosophila cation channel trp1 in recombinant baculovirus-infected Sf9 insect cells. Am. J. Physiol. 269, C1332–C1339.
47. Harteneck, C., Obukhov, A. G., Zobel, A., Kalkbrenner, F., and Schultz, G. (1995). The Drosophila cation channel trp1 in insect Sf9 cells is stimulated by agonists of G protein-coupled receptors. FEBS Lett. 358, 297–300.
48. Hu, Y. and Schilling, W. P. (1995). Receptor-mediated activation of recombinant trp1 expressed in Sf9 insect cells. Biochem. J. 305, 605–611.
49. Sanger, F., Nicklen, S., and Coulson, A. R. (1977). DNA sequencing with chain-terminating inhibitors. Proc. Natl. Acad. Sci. USA 74, 5463–5467.
50. Rudolph, U., Brabet, P., Hasty, P., Bradley, A., and Birnbaumer, L. (1993). Disruption of the $G_{i2}\alpha$ locus in embryonic stem cells and mice. Modified hit and run strategy with detection by PCR dependent on gap repair. Transgenic Res. 2, 345–355.
51. Daly, J. W., Lueders, J., Padget, W., Shin, Y. and Gusovsky, F. (1995). Maitotoxin-elicited Calcium Influx in Cultured Cells. Effect of Calcium Channel Blockers. Biochem. Pharmacol. 50, 1187–1197.
52. Merritt, J. E., Armstrong, W. P., Benham, C. D., Hallam, T. J., Jacob., R., Jaxa-Chamiec, A., Leigh, B. K., McCarthy, S. A., Moores, K. E. and Rink, T. J. (1990). SK&F 96365, A Novel Inhibitor of Receptor-mediated Calcium Entry. Biochem. J. 271, 515–522.

53. Low, A. M., Berdik, M., Sormaz, L., Gataiance, S., Buchanan, M. R., Kwan, C. Y. and Daniel., E. E. (1996). Plant alkaloids, Tetrandine and Hernandezine, Inhibit Calcium-Depletion Stimulated Calcium Entry in Human and Bovine Endothelial Cells. Life Sciences 58, 2327–2335.

54. Worley, J. F., McIntyre, M. S., Spencer, B. and Dukes, I. D. (1994). Depletion of Intracellular $Ca^{2+}$ Stores Acxtivates a Maitotoxin Sensitive Nonselective Cationic Current in β-Cells. J. Biol. Chem. 269, 32055–32058.

55. Partiseti, M., La Deist, F., Hivroz, C., Fischer, A., Korn, H. and Choquet, D. (1994). The Calcium Current Activated by T Cell Receptor and Store Depletion in Human Lymphocytes Is Absent in a Primary Immunodeficiency. J. Biol. Chem. 269, 32327–32335.

56. Le Deist, F., Hivroz, Partiseti, M., Thomas, C., Buc, H. A., Oleastro, M., Belohradsky,B. Choquet, D. and Fischer, A. (1995). A Primary T-Cell Immunodeficiency Associated With Defective Transmembrane Calcium Influx. Blood 85, 1053–1062.

57. Innamorati, G., Sadeghi, H. and Birnbaumer, M. (1996). A Fully Active Non-Glycosylated V2 Vasopressin Receptor. Mol. Pharmacol. 50, 467–473.

58. Gudermann, T., Birnbaumer, M. and Birnbaumer, L. (1992). Evidence for Dual Coupling of the Murine LH Receptor to Adenylyl Cyclase and Phosphoinositide Breakdown/$Ca^{2+}$ Mobilization. Studies with the Cloned Murine LH Receptor Expressed in L Cells. J. Biol. Chem. 267, 4479–4488.

59. Zhu, X., Gilbert, S., Birnbaumer, M. and Birnbaumer, L. (1994). Dual Signaling Potential is Common Among $G_s$-Coupled Receptors And Dependent on Receptor Density. Mol. Pharmacol. 46, 460–469.

We claim:

1. A method of screening a compound for controlling capacitative calcium ion entry into mammalian cells, said method comprising the steps of:

provisioning a cell culture which expresses a transient receptor potential protein which is selected from the group consisting of Htrm1 and Htrp3, said cell expressing said transient receptor potential protein to provide a naturally occurring level of biologically active transient receptor potential protein associated with said cell;

exposing said cell culture to said compound; and determining if the exposure of said cell culture to said compound increases or decreases the expression of said transient receptor potential protein to thereby provide an indication of the compound's potential use in controlling capacitative calcium ion entry into mammalian cells.

2. The method of claim 1, wherein the compound is a nucleotide sequence.

3. The method of claim 1, wherein the compound is an inhibitor.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 3290 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (A) ORGANISM:
      (C) INDIVIDUAL ISOLATE: Mtrp4

(xi) SEQUENCE DESCRIPTION: SEQ ID NO:1:

```
          ACCAGATTGC AACTTTGCGG AGATGATGAT GGACTGACAT GGCCTGAAGC              50

ATG GCT CAG TTC TAT TAC AAA AGA AAT GTC AAC GCC CCC TAC AGA GAC              98
Met Ala Gln Phe Tyr Tyr Lys Arg Asn Val Asn Ala Pro Tyr Arg Asp
1               5                   10                  15

CGC ATC CCA CTG AGG ATT GTC AGA GCA GAA TCT GAG CTC TCA CCA TCA             146
Arg Ile Pro Leu Arg Ile Val Arg Ala Glu Ser Glu Leu Ser Pro Ser
                20                  25                  30

GAG AAA GCC TAC TTG AAT GCT GTG GAG AAG GGG GAC TAT GCA AGC GTC             194
Glu Lys Ala Tyr Leu Asn Ala Val Glu Lys Gly Asp Tyr Ala Ser Val
            35                  40                  45

AAG AAG TCT CTG GAG GAA GCT GAG ATT TAT TTT AAA ATC AAC ATT AAC             242
Lys Lys Ser Leu Glu Glu Ala Glu Ile Tyr Phe Lys Ile Asn Ile Asn
        50                  55                  60

TGC ATC GAC CCC CTG GGA AGG ACC GCC CTC CTC ATT GCC ATT GAA AAT             290
Cys Ile Asp Pro Leu Gly Arg Thr Ala Leu Leu Ile Ala Ile Glu Asn
65                  70                  75                  80

GAG AAT CTG GAG CTT ATT GAA CTA TTG TTG AGT TTC AAT GTC TAT GTA             338
Glu Asn Leu Glu Leu Ile Glu Leu Leu Leu Ser Phe Asn Val Tyr Val
                85                  90                  95

GGC GAT GCG CTG CTT CAC GCC ATC AGA AAA GAG GTG GTT GGA GCC GTG             386
Gly Asp Ala Leu Leu His Ala Ile Arg Lys Glu Val Val Gly Ala Val
                100                 105                 110
```

```
GAG CTA CTG CTG AAC CAC AAA AAG CCA AGT GGA GAG AAG CAG GTG CCT        434
Glu Leu Leu Leu Asn His Lys Lys Pro Ser Gly Glu Lys Gln Val Pro
            115                 120                 125

CCC ATT CTC CTT GAT AAA CAG TTC TCT GAA TTC ACT CCG GAC ATC ACA        482
Pro Ile Leu Leu Asp Lys Gln Phe Ser Glu Phe Thr Pro Asp Ile Thr
130                 135                 140

CCC ATC ATC TTG GCT GCA CAT ACA AAT AAT TAC GAG ATA ATC AAA CTT        530
Pro Ile Ile Leu Ala Ala His Thr Asn Asn Tyr Glu Ile Ile Lys Leu
145                 150                 155                 160

TTG GTT CAG AAA GGT GTC TCA GTG CCC AGA CCC CAC GAG GTC CGC TGT        578
Leu Val Gln Lys Gly Val Ser Val Pro Arg Pro His Glu Val Arg Cys
                165                 170                 175

AAC TGT GTT GAG TGT GTC TCC AGC TCG GAT GTG GAC AGC CTC AGG CAT        626
Asn Cys Val Glu Cys Val Ser Ser Ser Asp Val Asp Ser Leu Arg His
                180                 185                 190

TCA CGG TCC AGG CTC AAC ATC TAC AAG GCC TTG GCC AGC CCC TCG CTC        674
Ser Arg Ser Arg Leu Asn Ile Tyr Lys Ala Leu Ala Ser Pro Ser Leu
            195                 200                 205

ATT GCC CTG TCA AGC GAA GAC CCT TTC CTT ACT GCC TTT CAG TTA AGT        722
Ile Ala Leu Ser Ser Glu Asp Pro Phe Leu Thr Ala Phe Gln Leu Ser
210                 215                 220

TGG GAG CTG CAA GAA CTC AGC AAG GTG GAG AAC GAA TTC AAG TCG GAG        770
Trp Glu Leu Gln Glu Leu Ser Lys Val Glu Asn Glu Phe Lys Ser Glu
225                 230                 235                 240

TAT GAG GAG CTG TCT AGA CAG TGC AAA CAA TTT GCC AAG GAC CTC CTA        818
Tyr Glu Glu Leu Ser Arg Gln Cys Lys Gln Phe Ala Lys Asp Leu Leu
                245                 250                 255

GAT CAG ACA CGG AGT TCC AGA GAG CTG GAA ATC ATT CTT AAT TAC CGT        866
Asp Gln Thr Arg Ser Ser Arg Glu Leu Glu Ile Ile Leu Asn Tyr Arg
            260                 265                 270

GAT GAC AaT AGT CTG ATC GAA GAA CAG AGT GGA AAT GAT CTT GCA AGG        914
Asp Asp Asn Ser Leu Ile Glu Glu Gln Ser Gly Asn Asp Leu Ala Arg
            275                 280                 285

CTA AAA TTA GCC ATT AAG TAC CGT CAA AAA GAG TTT GTT GCT CAG CCC        962
Leu Lys Leu Ala Ile Lys Tyr Arg Gln Lys Glu Phe Val Ala Gln Pro
290                 295                 300

AAC TGC CAG CAG CTG CTC GCT TCC CGC TGG TAC GAT GAG TTC CCA GGC       1010
Asn Cys Gln Gln Leu Leu Ala Ser Arg Trp Tyr Asp Glu Phe Pro Gly
305                 310                 315                 320

TGG AGG AGA AGA CAC TGG GCG GTG AAG ATG GTG ACG TGT TTC ATA ATA       1058
Trp Arg Arg Arg His Trp Ala Val Lys Met Val Thr Cys Phe Ile Ile
                325                 330                 335

GGA CTA CTC TTC CCC GTC TTC TCC GTG TGC TAC CTG ATA GCT CCC AAA       1106
Gly Leu Leu Phe Pro Val Phe Ser Val Cys Tyr Leu Ile Ala Pro Lys
            340                 345                 350

AGC CCA CTT GGA CTG TTC ATC AGa AAG CCA TTT ATC AAG TTT ATC TGC       1154
Ser Pro Leu Gly Leu Phe Ile Arg Lys Pro Phe Ile Lys Phe Ile Cys
            355                 360                 365

CAC ACA GCC TCC TAT CTG ACC TTT TTG TTT CTG CTG CTG CTA GCC TCT       1202
His Thr Ala Ser Tyr Leu Thr Phe Leu Phe Leu Leu Leu Leu Ala Ser
370                 375                 380

CAG CAC ATC GAC AGG TCA GAC TTG AAC AGG CAA GGT CCA CCA CCA ACC       1250
Gln His Ile Asp Arg Ser Asp Leu Asn Arg Gln Gly Pro Pro Pro Thr
385                 390                 395                 400

ATC GTG GAG TGG ATG ATA TTA CCG TGG GTC CTG GGT TTT ATA TGG GGA       1298
Ile Val Glu Trp Met Ile Leu Pro Trp Val Leu Gly Phe Ile Trp Gly
                405                 410                 415

GAG ATT AAA CAG ATG TGG GAT GGC GGA CTC CAG GAT TAC ATC CAT GAC       1346
Glu Ile Lys Gln Met Trp Asp Gly Gly Leu Gln Asp Tyr Ile His Asp
                420                 425                 430
```

-continued

| | |
|---|---|
| TGG TGG AAT CTA ATG GAC TTT GTG ATG AAC TCC TTG TAT CTG GCA ACA<br>Trp Trp Asn Leu Met Asp Phe Val Met Asn Ser Leu Tyr Leu Ala Thr<br>435              440              445 | 1394 |
| ATC TCC TTG AAG ATT GTC GCG TTT GTA AAG TAC AGT GCT CTG AAC CCA<br>Ile Ser Leu Lys Ile Val Ala Phe Val Lys Tyr Ser Ala Leu Asn Pro<br>450              455              460 | 1442 |
| CGG GAA TCA TGG GAC ATG TGG CAC CCC ACC CTG GTG GCA GAG GCA TTA<br>Arg Glu Ser Trp Asp Met Trp His Pro Thr Leu Val Ala Glu Ala Leu<br>465              470              475              480 | 1490 |
| TTT GCT ATT GCA AAC ATC TTC AGT TCC CTC CGC CTG ATC TCT CTG TTC<br>Phe Ala Ile Ala Asn Ile Phe Ser Ser Leu Arg Leu Ile Ser Leu Phe<br>485              490              495 | 1538 |
| ACT GCC AAT TCT CAC CTG GGG CCT CTG CAG ATA TCT CTG GGA AGG ATG<br>Thr Ala Asn Ser His Leu Gly Pro Leu Gln Ile Ser Leu Gly Arg Met<br>500              505              510 | 1586 |
| CTT CTG GAC ATC CTG AAG TTC TTG TTC ATC TAC TGC CTC GTG CTG CTA<br>Leu Leu Asp Ile Leu Lys Phe Leu Phe Ile Tyr Cys Leu Val Leu Leu<br>515              520              525 | 1634 |
| GCT TTT GCA AAT GGC CTA AAT CAG CTG TAC TTT TAC TAT GAA GAA ACA<br>Ala Phe Ala Asn Gly Leu Asn Gln Leu Tyr Phe Tyr Tyr Glu Glu Thr<br>530              535              540 | 1682 |
| AAG GGG CTA AGC TGC AAA GGC ATC CGG TGC GAG AAA CAG AAC AAC GCG<br>Lys Gly Leu Ser Cys Lys Gly Ile Arg Cys Glu Lys Gln Asn Asn Ala<br>545              550              555              560 | 1730 |
| TTT TCC ACG TTA TTC GAG ACA CTA CAG TCC CTG TTT TGG TCA ATA TTT<br>Phe Ser Thr Leu Phe Glu Thr Leu Gln Ser Leu Phe Trp Ser Ile Phe<br>565              570              575 | 1778 |
| GGA CTC ATC AAT CTC TAT GTT ACC AAT GTC AAG GCC CAG CAC GAG TTC<br>Gly Leu Ile Asn Leu Tyr Val Thr Asn Val Lys Ala Gln His Glu Phe<br>580              585              590 | 1826 |
| ACT GAG TTT GTT GGG GCC ACC ATG TTT GGC ACA TAT AAT GTC ATC TCT<br>Thr Glu Phe Val Gly Ala Thr Met Phe Gly Thr Tyr Asn Val Ile Ser<br>595              600              605 | 1874 |
| CTG GTT GTC CTG CTG AAC ATG TTA ATT GCT ATG ATG AAT AAT TCT TAC<br>Leu Val Val Leu Leu Asn Met Leu Ile Ala Met Met Asn Asn Ser Tyr<br>610              615              620 | 1922 |
| CAA CTA ATT GCC GAC CAT GCA GAT ATA GAA TGG AAA TTT GCT CGA ACA<br>Gln Leu Ile Ala Asp His Ala Asp Ile Glu Trp Lys Phe Ala Arg Thr<br>625              630              635              640 | 1970 |
| AAG CTT TGG ATG AGC TAC TTT GAA GAA GGA GGT ACC CTG CCT ACA CCT<br>Lys Leu Trp Met Ser Tyr Phe Glu Glu Gly Gly Thr Leu Pro Thr Pro<br>645              650              655 | 2018 |
| TTC AAT GTC ATC CCA AGC CCC AAG TCC CTG TGG TAC CTG GTC AAG TGG<br>Phe Asn Val Ile Pro Ser Pro Lys Ser Leu Trp Tyr Leu Val Lys Trp<br>660              665              670 | 2066 |
| ATA TGG ACA CAC TTA TGT AAG AAA AAA ATG AGA AGG AAG CCA GAA AGC<br>Ile Trp Thr His Leu Cys Lys Lys Lys Met Arg Arg Lys Pro Glu Ser<br>675              680              685 | 2114 |
| TTC GGG ACA ATT GGG CGG CTT GCT GCT GAT AAC TTG AGA AGA CAT CAC<br>Phe Gly Thr Ile Gly Arg Leu Ala Ala Asp Asn Leu Arg Arg His His<br>690              695              700 | 2162 |
| CAA TAC CAA GAG GTG ATG AGG AAC CTG GTG AAG CGG TAC GTG GCT GCC<br>Gln Tyr Gln Glu Val Met Arg Asn Leu Val Lys Arg Tyr Val Ala Ala<br>705              710              715              720 | 2210 |
| ATG ATC AGA GAG GCA AAA ACC GAA GAA GGC TTG ACG GAG GAG AAT GTT<br>Met Ile Arg Glu Ala Lys Thr Glu Glu Gly Leu Thr Glu Glu Asn Val<br>725              730              735 | 2258 |
| AAG GAA CTA AAG CAA GAC ATT TCT AGC TTC CGC TTC GAA GTT CTG GGA<br>Lys Glu Leu Lys Gln Asp Ile Ser Ser Phe Arg Phe Glu Val Leu Gly<br>740              745              750 | 2306 |

```
TTG CTC AGA GGA AGC AAG CTC TCT ACA ATA CAG TCA GCC AAC GCG GCG           2354
Leu Leu Arg Gly Ser Lys Leu Ser Thr Ile Gln Ser Ala Asn Ala Ala
        755                 760                 765

AGT TCA GCG GAC TCC GAC GAG AAG AGC CAG AGC GAA GGT AAT GGC AAG           2402
Ser Ser Ala Asp Ser Asp Glu Lys Ser Gln Ser Glu Gly Asn Gly Lys
770                 775                 780

GAC AAG AGA AAG AAT CTC AGC CTC TTT GAT TTA ACC ACT CTG ATC TAC           2450
Asp Lys Arg Lys Asn Leu Ser Leu Phe Asp Leu Thr Thr Leu Ile Tyr
785                 790                 795                 800

CCG CGG TCG GCA GCC ATT GCC TCC GAG AGA CAT AAC CTA AGC AAT GGT           2498
Pro Arg Ser Ala Ala Ile Ala Ser Glu Arg His Asn Leu Ser Asn Gly
                805                 810                 815

TCC GCC CTG GTG GTG CAG GAG CCG CCC AGG GAG AAG CAG AGG AAA GTG           2546
Ser Ala Leu Val Val Gln Glu Pro Pro Arg Glu Lys Gln Arg Lys Val
            820                 825                 830

AAT TTT GTG GCT GAT ATC AAA AAC TTC GGG TTA TTT CAT AGA CGG TCA           2594
Asn Phe Val Ala Asp Ile Lys Asn Phe Gly Leu Phe His Arg Arg Ser
                835                 840                 845

AAA CAA AAT GCT GCT GAG CAA AAC GCA AAC CAA ATC TTC TCT GTT TCA           2642
Lys Gln Asn Ala Ala Glu Gln Asn Ala Asn Gln Ile Phe Ser Val Ser
850                 855                 860

GAA GAA ATT ACT CGT CAA CAG GCG GCA GGA GCA CTT GAG CGA AAT ATC           2690
Glu Glu Ile Thr Arg Gln Gln Ala Ala Gly Ala Leu Glu Arg Asn Ile
865                 870                 875                 880

GAA CTG GAA TCC AAA GGA TTA GCT TCA CTG GGT GAC CGC AGC ATT CCT           2738
Glu Leu Glu Ser Lys Gly Leu Ala Ser Leu Gly Asp Arg Ser Ile Pro
                885                 890                 895

GGT CTC AAT GAA CAG TGT GTG CTA GTA GAC CAT AGA GAA AGG AAT ACG           2786
Gly Leu Asn Glu Gln Cys Val Leu Val Asp His Arg Glu Arg Asn Thr
            900                 905                 910

GAC ACT TTG GGT TTA CAG GTA GGC AAG AGA GTG TGC TCC ACC TTC AAG           2834
Asp Thr Leu Gly Leu Gln Val Gly Lys Arg Val Cys Ser Thr Phe Lys
        915                 920                 925

TCG GAG AAG GTG GTG GTG GAA GAC ACC GTC CCT ATT ATA CCA AAG GAG           2882
Ser Glu Lys Val Val Val Glu Asp Thr Val Pro Ile Ile Pro Lys Glu
    930                 935                 940

AAA CAC GCC CAT GAG GAG GAC TCG AGC ATA GAC TAT GAC TTA AGC CCC           2930
Lys His Ala His Glu Glu Asp Ser Ser Ile Asp Tyr Asp Leu Ser Pro
945                 950                 955                 960

ACG GAC ACA GCT GCC CAT GAA GAT TAT GTG ACC ACA AGA TTG                   2972
Thr Asp Thr Ala Ala His Glu Asp Tyr Val Thr Thr Arg Leu
                965                 970             974

TGACCCTTGG AGGAGTGTTT ACCATACCTA TACATATTTT CCATAGTGCT CTGAGCAGGC         3032

AAAATGTTTG AAATCCCATT ATCAAATGCT AATTTCCACT TTCTAATGTT TATCTGTTGT         3092

GGCATATTAA CCTGTAATAT GTTTGAACAA AGCAGAGGTA ATATGAACCC TTCTCTTTTG         3152

TAGCCTGCTT TTGCTTTCAC CGTTTATTTT ACAAGTGTTT CTGTTAAATA AACGCACCTT         3212

TTCTCCTTGT ACTGTTACAA TAACCCACAG AAAACTTTTA GCTATCTTTT TTCAATTAAA         3272

ACCAATGCAA TTGTTTTC                                                       3290
```

(2) INFORMATION FOR SEQ ID NO:2:

(i) SEQUENCE CHARACTERISTICS:
        (A) LENGTH: 3258 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
    (A) ORGANISM:
    (C) INDIVIDUAL ISOLATE: Mtrp4

(xi) SEQUENCE DESCRIPTION: SEQ ID NO:2:

```
CGCCTGTGCC CTCTGCCTGG GAGCCTGGGG CCGCCTGTCT GCGCGGTCCG GATGCGCTCA      60

GGTCAAGGTT CCTTTCGCGG CTGTCTCCCA AGCCCCTAAC TAGTGACTTC CACTGTGGCG     120

GGCAGGGAAG CCATTGGCAG AACCTAGCCA GTCAGGAATC TGCATCTCTT CCCTCATTAT     180

CCTCTCCCTG GCATTGCTTT GCTCGGGTCC AGCTCAGTTG GTGACGCGGC CCCTTCTCCC     240

CAGGTTCCCA TCCACGGAAG CAGGGGTGCA GGCCGGCCAG GCACTGTGCC                290

ATG AGC CAG AGC CCG AGG TTC GTG ACC CGG AGG GGC GGC TCT CTA AAG      338
Met Ser Gln Ser Pro Arg Phe Val Thr Arg Arg Gly Gly Ser Leu Lys
             5                  10                  15

GCT GCC CCT GGA GCC GGC ACC CGG CGC AAC GAG AGC CAG GAC TAT TTG      386
Ala Ala Pro Gly Ala Gly Thr Arg Arg Asn Glu Ser Gln Asp Tyr Leu
         20                  25                  30

CTG ATG GAC GAG CTG GGA GAC GAC GGC TAC CCG CAG CTC CCG CTG CCA      434
Leu Met Asp Glu Leu Gly Asp Asp Gly Tyr Pro Gln Leu Pro Leu Pro
     35                  40                  45

CCG TAT GGC TAC TAC CCC AGC TTC CGG GGT AAT GAA AAC AGA CTG ACT      482
Pro Tyr Gly Tyr Tyr Pro Ser Phe Arg Gly Asn Glu Asn Arg Leu Thr
 50                  55                  60

CAC CGG CGG CAG ACG ATT CTT CGT GAG AAG GGA AGA AGG TTA GCT AAT      530
His Arg Arg Gln Thr Ile Leu Arg Glu Lys Gly Arg Arg Leu Ala Asn
 65                  70                  75                  80

CGA GGA CCA GCA TAC ATG TTT AAT GAT CAT TCA ACA AGC CTG TCT ATT      578
Arg Gly Pro Ala Tyr Met Phe Asn Asp His Ser Thr Ser Leu Ser Ile
                 85                  90                  95

GAG GAA GAA CGC TTT CTA GAT GCA GCT GAA TAT GGC AAC ATC CCA GTG      626
Glu Glu Glu Arg Phe Leu Asp Ala Ala Glu Tyr Gly Asn Ile Pro Val
            100                 105                 110

GTG CGG AAG ATG CTA GAA GAG TGT CAT TCC CTC AAT GTT AAC TGT GTG      674
Val Arg Lys Met Leu Glu Glu Cys His Ser Leu Asn Val Asn Cys Val
        115                 120                 125

GAT TAC ATG GGC CAG AAT GCC CTA CAG CTG GCT GTG GCC AAT GAG CAC      722
Asp Tyr Met Gly Gln Asn Ala Leu Gln Leu Ala Val Ala Asn Glu His
    130                 135                 140

TTG GAA ATC ACA GAG CTG CTA CTC AAG AAG GAA AAC TTG TCT CGA GTT      770
Leu Glu Ile Thr Glu Leu Leu Leu Lys Lys Glu Asn Leu Ser Arg Val
145                 150                 155                 160

GGG GAT GCT TTA CTT TTA GCC ATT AGT AAA GGT TAT GTA CGG ATT GTG      818
Gly Asp Ala Leu Leu Leu Ala Ile Ser Lys Gly Tyr Val Arg Ile Val
                165                 170                 175

GAG GCA ATC CTC AAC CAT CCA GCT TTT GCT GAA GGC AAA AGG TTA GCG      866
Glu Ala Ile Leu Asn His Pro Ala Phe Ala Glu Gly Lys Arg Leu Ala
            180                 185                 190

ACA AGC CCC AGC CAG TCT GAA CTT CAG CAA GAT GAC TTT TAT GCC TAT      914
Thr Ser Pro Ser Gln Ser Glu Leu Gln Gln Asp Asp Phe Tyr Ala Tyr
        195                 200                 205

GAT GAA GAT GGG ACG CGG TTC TCC CAT GAT GTG ACC CCA ATC ATT CTC      962
Asp Glu Asp Gly Thr Arg Phe Ser His Asp Val Thr Pro Ile Ile Leu
    210                 215                 220

GCT GCA CAT TGC CAG GAA TAT GAA ATT GTG CAT ACC CTC CTG AGA AAG     1010
Ala Ala His Cys Gln Glu Tyr Glu Ile Val His Thr Leu Leu Arg Lys
225                 230                 235                 240
```

| | | |
|---|---|---|
| GGT GCC CGG ATT GAG CGG CCT CAT GAT TAC TTC TGC AAG TGT ACA GAA<br>Gly Ala Arg Ile Glu Arg Pro His Asp Tyr Phe Cys Lys Cys Thr Glu<br>245 250 255 | | 1058 |
| TGC AGC CAG AAG CAG AAG CAT GAT TCC TTC AGC CAC TCT AGA TCC AGG<br>Cys Ser Gln Lys Gln Lys His Asp Ser Phe Ser His Ser Arg Ser Arg<br>260 265 270 | | 1106 |
| ATC AAT GCA TAC AAA GGT CTG GCA AGT CCA GCA TAC CTG TCA TTG TCC<br>Ile Asn Ala Tyr Lys Gly Leu Ala Ser Pro Ala Tyr Leu Ser Leu Ser<br>275 280 285 | | 1154 |
| AGT GAA GAT CCA GTC ATG ACT GCT TTA GAA CTT AGC AAT GAG CTG GCA<br>Ser Glu Asp Pro Val Met Thr Ala Leu Glu Leu Ser Asn Glu Leu Ala<br>290 295 300 | | 1202 |
| GTG CTT GCC AAC ATT GAG AAA GAG TTC AAG AAT GAC TAC AGG AAG CTG<br>Val Leu Ala Asn Ile Glu Lys Glu Phe Lys Asn Asp Tyr Arg Lys Leu<br>305 310 315 320 | | 1250 |
| TCT ATG CAG TGC AAG GAT TTC GTT GTT GGT CTC TTG GAC CTC TGC AGA<br>Ser Met Gln Cys Lys Asp Phe Val Val Gly Leu Leu Asp Leu Cys Arg<br>325 330 335 | | 1298 |
| AAC ACA GAG GAA GTG GAG GCC ATC CTG AAT GGG GAT GCA GAG ACT CGC<br>Asn Thr Glu Glu Val Glu Ala Ile Leu Asn Gly Asp Ala Glu Thr Arg<br>340 345 350 | | 1346 |
| CAG CCC GGG GAC TTC GGC CGT CCA AAT CTC AGC CGT TTA AAA CTT GCT<br>Gln Pro Gly Asp Phe Gly Arg Pro Asn Leu Ser Arg Leu Lys Leu Ala<br>355 360 365 | | 1394 |
| ATT AAG TAT GAA GTA AAA AAA TTT GTG GCT CAT CCA AAC TGT CAG CAA<br>Ile Lys Tyr Glu Val Lys Lys Phe Val Ala His Pro Asn Cys Gln Gln<br>370 375 380 | | 1442 |
| CAG CTC CTG TCC ATA TGG TAT GAG AAC CTC TCT GGT TTA CGG CAG CAG<br>Gln Leu Leu Ser Ile Trp Tyr Glu Asn Leu Ser Gly Leu Arg Gln Gln<br>385 390 395 400 | | 1490 |
| ACC ATG GCA GTG AAG TTC CTC GTG GTC CTT GCT GTT GCC ATT GGA TTG<br>Thr Met Ala Val Lys Phe Leu Val Val Leu Ala Val Ala Ile Gly Leu<br>405 410 415 | | 1538 |
| CCC TTC CTG GCT CTC ATA TAC TGG TGT GCT CCT TGC AGC AAG ATG GGG<br>Pro Phe Leu Ala Leu Ile Tyr Trp Cys Ala Pro Cys Ser Lys Met Gly<br>420 425 430 | | 1586 |
| AAG ATA TTG CGA GGA CCG TTC ATG AAG TTT GTA GCA CAC GCA GCC TCC<br>Lys Ile Leu Arg Gly Pro Phe Met Lys Phe Val Ala His Ala Ala Ser<br>435 440 445 | | 1634 |
| TTC ACC ATT TTC CTG GGG CTG CTC GTC ATG AAT GCA GCT GAC AGA TTT<br>Phe Thr Ile Phe Leu Gly Leu Leu Val Met Asn Ala Ala Asp Arg Phe<br>450 455 460 | | 1682 |
| GAA GGC ACC AAG CTC CTC CCT AAT GAA ACC AGC ACA GAT AAT GCA AGG<br>Glu Gly Thr Lys Leu Leu Pro Asn Glu Thr Ser Thr Asp Asn Ala Arg<br>465 470 475 480 | | 1730 |
| CAG CTG TTC AGG ATG AAA ACA TCC TGT TTC TCA TGG ATG GAG ATG CTC<br>Gln Leu Phe Arg Met Lys Thr Ser Cys Phe Ser Trp Met Glu Met Leu<br>485 490 495 | | 1778 |
| ATT ATA TCC TGG GTA ATA GGC ATG ATA TGG GCT GAA TGT AAA GAA ATC<br>Ile Ile Ser Trp Val Ile Gly Met Ile Trp Ala Glu Cys Lys Glu Ile<br>500 505 510 | | 1826 |
| TGG ACT CAA GGC CCC AAA GAA TAC TTA TTT GAG TTG TGG AAT ATG CTT<br>Trp Thr Gln Gly Pro Lys Glu Tyr Leu Phe Glu Leu Trp Asn Met Leu<br>515 520 525 | | 1874 |
| GAC TTT GGA ATG CTG GCA ATC TTT GCA GCA TCA TTC ATT GCA AGA TTT<br>Asp Phe Gly Met Leu Ala Ile Phe Ala Ala Ser Phe Ile Ala Arg Phe<br>530 535 540 | | 1922 |
| ATG GCG TTC TGG CAT GCA TCC AAA GCT CAG AGC ATC ATT GAT GCA AAT<br>Met Ala Phe Trp His Ala Ser Lys Ala Gln Ser Ile Ile Asp Ala Asn<br>545 550 555 560 | | 1970 |

```
GAT ACT TTA AAG GAT TTG ACA AAA GTC ACA CTG GGG GAC AAC GTT AAA         2018
Asp Thr Leu Lys Asp Leu Thr Lys Val Thr Leu Gly Asp Asn Val Lys
            565                 570                 575

TAC TAC AAT CTG GCC AGG ATA AAG TGG GAC CCT ACT GAT CCT CAG ATC         2066
Tyr Tyr Asn Leu Ala Arg Ile Lys Trp Asp Pro Thr Asp Pro Gln Ile
            580                 585                 590

ATC TCT GAA GGT CTT TAT GCA ATC GCT GTG GTT TTA AGT TTC TCC AGA         2114
Ile Ser Glu Gly Leu Tyr Ala Ile Ala Val Val Leu Ser Phe Ser Arg
            595                 600                 605

ATA GCT TAC ATT TTA CCA GCA AAT GAA AGC TTT GGA CCT CTG CAG ATT         2162
Ile Ala Tyr Ile Leu Pro Ala Asn Glu Ser Phe Gly Pro Leu Gln Ile
            610                 615                 620

TCA CTT GGA AGA ACA GTG AAA GAT ATC TTC AAA TTC ATG GTC ATA TTC         2210
Ser Leu Gly Arg Thr Val Lys Asp Ile Phe Lys Phe Met Val Ile Phe
625                 630                 635                 640

ATC ATG GTG TTT GTA GCC TTT ATG ATT GGA ATG TTC AAC CTT TAC TCC         2258
Ile Met Val Phe Val Ala Phe Met Ile Gly Met Phe Asn Leu Tyr Ser
                    645                 650                 655

TAC TAC ATT GGC GCA AAA CAG AAT GAA GCA TTC ACA ACA GTT GAG GAA         2306
Tyr Tyr Ile Gly Ala Lys Gln Asn Glu Ala Phe Thr Thr Val Glu Glu
            660                 665                 670

AGT TTT AAG ACA CTG TTC TGG GCT ATC TTT GGT CTT TCT GAA GTG AAG         2354
Ser Phe Lys Thr Leu Phe Trp Ala Ile Phe Gly Leu Ser Glu Val Lys
            675                 680                 685

TCA GTG GTC ATT AAC TAC AAT CAC AAG TTC ATT GAA AAC ATC GGC TAC         2402
Ser Val Val Ile Asn Tyr Asn His Lys Phe Ile Glu Asn Ile Gly Tyr
        690                 695                 700

GTT CTG TAT GGT GTC TAT AAT GTC ACA ATG GTC ATT GTT TTG CTA AAT         2450
Val Leu Tyr Gly Val Tyr Asn Val Thr Met Val Ile Val Leu Leu Asn
705                 710                 715                 720

ATG TTA ATT GCG ATG ATC AAT AGT TCA TTC CAG GAA ATT GAG GAT GAT         2498
Met Leu Ile Ala Met Ile Asn Ser Ser Phe Gln Glu Ile Glu Asp Asp
                    725                 730                 735

GCG GAC GTG GAG TGG AAG TTT GCA AGG GCC AAA TTG TGG TTT TCC TAC         2546
Ala Asp Val Glu Trp Lys Phe Ala Arg Ala Lys Leu Trp Phe Ser Tyr
            740                 745                 750

TTT GAG GAG GGG AGA ACA CTT CCT GTC CCC TTC AAT CTT GTA CCA AGT         2594
Phe Glu Glu Gly Arg Thr Leu Pro Val Pro Phe Asn Leu Val Pro Ser
            755                 760                 765

CCA AAA TCC TTG CTT TAT CTC CTA TTG AAA TTT AAG AAA TGG ATG TGT         2642
Pro Lys Ser Leu Leu Tyr Leu Leu Leu Lys Phe Lys Lys Trp Met Cys
770                 775                 780

GAG CTC ATC CAG GGT CAA AAG CAA GGC TTC CAA GAA GAT GCA GAG ATG         2690
Glu Leu Ile Gln Gly Gln Lys Gln Gly Phe Gln Glu Asp Ala Glu Met
785                 790                 795                 800

AAC AAG AGA AAT GAA GAA AAG AAA TTT GGA ATT TCA GGA AGT CAC GAA         2738
Asn Lys Arg Asn Glu Glu Lys Lys Phe Gly Ile Ser Gly Ser His Glu
            805                 810                 815

GAC CTT TCA AAA TTT TCA CTT GAC AAA AAT CAG TTG GCA CAC AAC AAA         2786
Asp Leu Ser Lys Phe Ser Leu Asp Lys Asn Gln Leu Ala His Asn Lys
            820                 825                 830

CAA TCA AGT ACA AGG AGC TCA GAA GAT TAT CAT TTA AAT AGT TTC AGT         2834
Gln Ser Ser Thr Arg Ser Ser Glu Asp Tyr His Leu Asn Ser Phe Ser
            835                 840                 845

AAC CCT CCA AGA CAA TAT CAG AAA ATC ATG AAG AGA CTC ATT AAA AGA         2882
Asn Pro Pro Arg Gln Tyr Gln Lys Ile Met Lys Arg Leu Ile Lys Arg
850                 855                 860

TAT GTA TTG CAG GCC CAG ATT GAT AAG GAG AGC GAT GAG GTG AAT GAA         2930
Tyr Val Leu Gln Ala Gln Ile Asp Lys Glu Ser Asp Glu Val Asn Glu
865                 870                 875                 880
```

-continued

```
GGG GAA TTG AAG GAA ATT AAG CAA GAC ATC TCA AGT CTC CGT TAT GAA    2978
Gly Glu Leu Lys Glu Ile Lys Gln Asp Ile Ser Ser Leu Arg Tyr Glu
                885                 890                 895

CTC CTT GAA GAG AAA TCA CAG AAC TCA GAA GAC CTA GCA GAG CTC ATT    3026
Leu Leu Glu Glu Lys Ser Gln Asn Ser Glu Asp Leu Ala Glu Leu Ile
            900                 905                 910

AGA AAA CTC GGG GAG AGA CTG TCG TTA GAG CCA AAG CTG GAG GAA AGC    3074
Arg Lys Leu Gly Glu Arg Leu Ser Leu Glu Pro Lys Leu Glu Glu Ser
        915                 920                 925

CGC AGA                                                            3080
Arg Arg
    930

AGCAGAGCCC CTCAGAAGTG CATATTTATT TCTCCACTTG AAGCCATATT ATTTTCTGAC  3140

TTATTTTTTT AAGTGTCAAT GATAAAAAGT ATGTTAACTG ATAACTTGGA TCATTTAGAG  3200

TCCTAATATC AAGCTTTTTG GGAGATTAAA TTGCATTGCT GAGGGCTAAC AATTGCTG    3258
```

(2) INFORMATION FOR SEQ ID NO:3:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:3:

```
TTGAACATAA ATTGCGTAGA TGTGCTTGGG AGAAATGCTG TTACC                    45
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:4:

```
TCGCACGCCA GCAAGAAAAG                                                20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO -continued (iv) ANTI-SENSE: NO (vi) ORIGINAL SOURCE:
         (A) ORGANISM:
         (C) INDIVIDUAL ISOLATE: Mtrp4

(xi) SEQUENCE DESCRIPTION: SEQ ID NO:5:

CGATGAGCAG CTAAAATGAC                                              20

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (A) ORGANISM:
         (C) INDIVIDUAL ISOLATE: Mtrp4

(xi) SEQUENCE DESCRIPTION: SEQ ID NO:6:

TGTCAGTCCA ATTGTGAAAG A                                            21

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (A) ORGANISM:
         (C) INDIVIDUAL ISOLATE: Mtrp4

(xi) SEQUENCE DESCRIPTION: SEQ ID NO:7:

TGACTTCCGT TGTGCTCAAA TATGATCACA AATTCATAG                          39

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
         (A) ORGANISM:
         (C) INDIVIDUAL ISOLATE: Mtrp4

(xi) SEQUENCE DESCRIPTION: SEQ ID NO:8:

ATGGAATATA CAATGTAACT ATGGTGGTCG                                    30

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:9:

```
GGACTAGGAA CTAGACTGAA AGGTGGAGGT AATGTTTTTC CATCATCA          48
```

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:10:

```
CGAGCAAACT TCCATTCTAC ATCACTGTC                               29
```

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:11:

```
GCNGARGGNC TCTTNGC                                            17
```

(2) INFORMATION FOR SEQ ID NO:12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA -continued

```
        (iii) HYPOTHETICAL: NO (iv) ANTI-SENSE: NO (vi) ORIGINAL SOURCE:
             (A) ORGANISM:
             (C) INDIVIDUAL ISOLATE: Mtrp4

(xi) SEQUENCE DESCRIPTION: SEQ ID NO:12:

CGNGCRAAYT GCARRT                                                    16

(2) INFORMATION FOR SEQ ID NO:13:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (A) ORGANISM:
             (C) INDIVIDUAL ISOLATE: Mtrp4

(xi) SEQUENCE DESCRIPTION: SEQ ID NO:13:

TGGGNCCNYT GCARRT                                                    16

(2) INFORMATION FOR SEQ ID NO:14:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (A) ORGANISM:
             (C) INDIVIDUAL ISOLATE: Mtrp4

(xi) SEQUENCE DESCRIPTION: SEQ ID NO:14:

CGNGCRAAYT TCCAYTC                                                   17

(2) INFORMATION FOR SEQ ID NO:15:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: NO (vi) ORIGINAL SOURCE:
             (A) ORGANISM:
             (C) INDIVIDUAL ISOLATE: Mtrp4

(xi) SEQUENCE DESCRIPTION: SEQ ID NO:15:

ACCTCTCAGG CCTAAGGGAG                                                20
```

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:16:

CCTTCTGAAG TCTTCTCCTT CTGC                                            24

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:17:

TCTGCAGATA TCTCTGGGAA GGATGC                                        26

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:18:

AAGCTTTGTT CGAGCAAATT TCCATTC                                     27

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
             (A) ORGANISM:
             (C) INDIVIDUAL ISOLATE: Mtrp4

(xi) SEQUENCE DESCRIPTION: SEQ ID NO:19:

AMRCCNTTYA TGAARTT                                                              17

(2) INFORMATION FOR SEQ ID NO:20:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (A) ORGANISM:
             (C) INDIVIDUAL ISOLATE: Mtrp4

(xi) SEQUENCE DESCRIPTION: SEQ ID NO:20:

CCACTCCACG TCCGCATCAT CC                                                        22

(2) INFORMATION FOR SEQ ID NO:21:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (A) ORGANISM:
             (C) INDIVIDUAL ISOLATE: Mtrp4

(xi) SEQUENCE DESCRIPTION: SEQ ID NO:21:

GGTTTAGCTA TGGGAAGAG C                                                          21

(2) INFORMATION FOR SEQ ID NO:22:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (vi) ORIGINAL SOURCE:
             (A) ORGANISM:
             (C) INDIVIDUAL ISOLATE: Mtrp4

(xi) SEQUENCE DESCRIPTION: SEQ ID NO:22:

TTTCCANTCT TTATCCTCAT G                                                      21

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:23:

TGGACATGCC TCAGTTCCTG G                                                      21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:24:

TTTCCANTCC ACATCAGCAT C                                                      21

(2) INFORMATION FOR SEQ ID NO:25:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:25:

GGCTATGTTC TTTATGGGAT AT                                                     22

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued (ii) MOLECULE TYPE: DNA (iii) HYPOTHETICAL: NO (iv) ANTI-SENSE: NO (vi) ORIGINAL SOURCE:
    (A) ORGANISM:
    (C) INDIVIDUAL ISOLATE: Mtrp4

(xi) SEQUENCE DESCRIPTION: SEQ ID NO:26:

```
CCATCATCAA AGTAGGAGAG CC                                    22
```

(2) INFORMATION FOR SEQ ID NO:27:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (A) ORGANISM:
    (C) INDIVIDUAL ISOLATE: Mtrp4

(xi) SEQUENCE DESCRIPTION: SEQ ID NO:27:

```
ATGTCAAAGC CCAGCACGAG T                                     21
```

(2) INFORMATION FOR SEQ ID NO:28:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (A) ORGANISM:
    (C) INDIVIDUAL ISOLATE: Mtrp4

(xi) SEQUENCE DESCRIPTION: SEQ ID NO:28:

```
AAGCTTTGTT CGAGCAAATT TCCATTC                               27
```

(2) INFORMATION FOR SEQ ID NO:29:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: NO (vi) ORIGINAL SOURCE:
    (A) ORGANISM:
    (C) INDIVIDUAL ISOLATE: Mtrp4

(xi) SEQUENCE DESCRIPTION: SEQ ID NO:29:

```
ATGTGAAGGC CGACATGAG T                                                    21

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:30:

TTTCCATTCA ATATCAGCAT G                                                   21

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:31:

ATCGGCTACG TTCTGTATGG TGTC                                                24

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (A) ORGANISM:
        (C) INDIVIDUAL ISOLATE: Mtrp4

(xi) SEQUENCE DESCRIPTION: SEQ ID NO:32:

GGAAAACCAC AATTTGGCCC TTGC                                                24
```